US012781201B2

(12) United States Patent
Xie et al.

(10) Patent No.: US 12,781,201 B2
(45) Date of Patent: Nov. 3, 2026

(54) MODIFIED GLUTAMATE DEHYDROGENASE AND APPLICATION THEREOF

(71) Applicant: Hunan Lier Biotech Co., Ltd., Jinshi (CN)

(72) Inventors: Xinkai Xie, Jiangsu (CN); Wei Xu, Jiangsu (CN); Junying Fan, Jiangsu (CN)

(73) Assignee: Hunan Lier Biotech Co., Ltd., Jinshi (CN)

( * ) Notice: Subject to any disclaimer, the term of this patent is extended or adjusted under 35 U.S.C. 154(b) by 222 days.

(21) Appl. No.: 18/725,181

(22) PCT Filed: Dec. 29, 2022

(86) PCT No.: PCT/CN2022/143241
§ 371 (c)(1),
(2) Date: Jun. 28, 2024

(87) PCT Pub. No.: WO2023/125769
PCT Pub. Date: Jul. 6, 2023

(65) Prior Publication Data

US 2025/0129344 A1 Apr. 24, 2025

(30) Foreign Application Priority Data

Dec. 31, 2021 (CN) ......................... 202111670071.9

(51) Int. Cl.
*C12N 9/06* (2006.01)
*C12P 13/04* (2006.01)

(52) U.S. Cl.
CPC ............ *C12N 9/0016* (2013.01); *C12P 13/04* (2013.01); *C12Y 104/01002* (2013.01)

(58) Field of Classification Search
None
See application file for complete search history.

(56) References Cited

FOREIGN PATENT DOCUMENTS

| | | |
|---|---|---|
| CN | 108588045 | 9/2018 |
| CN | 110184246 | 8/2019 |
| CN | 110343676 | 10/2019 |
| CN | 111979208 | 11/2020 |
| CN | 112553285 | 3/2021 |
| CN | 113088500 | 7/2021 |
| CN | 113088501 | 7/2021 |
| JP | 2004089097 | 3/2004 |
| WO | 2019192505 | 10/2019 |
| WO | 2020233451 | 11/2020 |

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
GenPept Database Accession No. WP_042351904, Jan. 2020, 1 page (Year: 2020).*
Cheng F, Li Q, Li H, Xue Y. NAD (P) H-dependent oxidoreductases for synthesis of chiral amines by asymmetric reductive amination of ketones. Sheng wu Gong Cheng xue bao= Chinese Journal of Biotechnology. Sep. 1, 2020;36(9):1794-816. (English Abstract).
NCBI, "NADP-specific glutamate dehydrogenase [*Lysinibacillus* sp. CD3-6]", NCBI Reference Sequence: WP_172771001.1,2021 年11月10日 (Nov. 10, 2021), 2 pages.
Yin X, Liu Y, Meng L, Zhou H, Wu J, Yang L. Rational molecular engineering of glutamate dehydrogenases for enhancing asymmetric reductive amination of bulky α-keto acids. Advanced Synthesis & Catalysis. Feb. 19, 2019;361(4):803-12.

* cited by examiner

*Primary Examiner* — David Steadman
(74) *Attorney, Agent, or Firm* — Robin L. Teskin; Baker, Donelson, Bearman, Caldwell & Berkowitz PC

(57) ABSTRACT

The present invention refers to a modified glutamate dehydrogenase (GluDH). In particular the modified GluDH of the present invention has an increased activity for catalyzing the reaction of 4-(hydroxymethylphosphinyl)-2-oxobutanoic acid (PPO) and an amino donor to generate L-glufosinate and/or an improved dynamic property. The present invention also refers to the polynucleotide encoding the modified GluDH of the present invention, the vector and host cell for expressing the modified GluDH of the present invention and the method of producing L-glufosinate with the modified GluDH and host cell of the present invention.

12 Claims, No Drawings

Specification includes a Sequence Listing.

SEQUENCE LISTING

```
Sequence total quantity: 80
SEQ ID NO: 1           moltype = AA  length = 457
FEATURE                Location/Qualifiers
source                 1..457
                       mol_type = protein
                       organism = Bacillus velezensis
SEQUENCE: 1
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDVPAGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                           457

SEQ ID NO: 2           moltype = AA  length = 457
FEATURE                Location/Qualifiers
source                 1..457
                       mol_type = protein
                       organism = Lysinibacillus sphaericus
SEQUENCE: 2
MTITTVSNEQ LAKEYVDGVF EQLKQQNCHQ AEFLQAAEEI FISLVPVFVQ HPEYIKANIL  60
SRIVEPDRII SFRVAWQDDH NQVQVNRGYR VQYSNVMGPY KGGLRFHPSV NESIIKFLGF  120
EQIFKNALTG QPIGGGKGGS NFDPKGKSDS EIMRFCQAFM TELYRHIGPD VDVPAGDIGV  180
GAREVGYLWG QYKRLTKASE SGVLTGKTPG YGGSLARKEA TGYGTVYFVN EMLKDVNDSF  240
EGKTVVVSGS GNVSTYAIEK AQQYGAKVVA CSDSSGYIYD PEGLDLDVIK EIKEVKGDRI  300
STYVSYRPNA TFTNGCTGIW TIPCDIALPC ATQNEINGES ARTLISNGVK AIGEGANMPS  360
DLEAINEFLN AGVLFGPAKA ANAGGVAVSA LEMAQDSSRV FWSFEEVDAK LHQIMKDIYS  420
DSKAAAEKYG FPGNLVMGAN IAGFIKVADG MLTEGIY                           457

SEQ ID NO: 3           moltype = AA  length = 457
FEATURE                Location/Qualifiers
source                 1..457
                       mol_type = protein
                       organism = synthetic construct
SEQUENCE: 3
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDVPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                           457

SEQ ID NO: 4           moltype = AA  length = 457
FEATURE                Location/Qualifiers
source                 1..457
                       mol_type = protein
                       organism = synthetic construct
SEQUENCE: 4
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGCRFHPSV NESIIKFLGF  120
EQIFKNALTG QPIGGGKGGS NFNPKGKSDS EIMRFCQAFM TELYRHIGPD VDVPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                           457

SEQ ID NO: 5           moltype = AA  length = 457
FEATURE                Location/Qualifiers
source                 1..457
                       mol_type = protein
                       organism = synthetic construct
SEQUENCE: 5
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLIGGGKGGS NFNPKGKSDS EIMRFCQAFM TELYRHIGPD VDVPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                           457

SEQ ID NO: 6           moltype = AA  length = 457
FEATURE                Location/Qualifiers
```

```
source                  1..457
                        mol_type = protein
                        organism = synthetic construct
SEQUENCE: 6
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPVGGGKGGS NFNPKGKSDS EIMRFCQAFM TELYRHIGPD VDVPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 7            moltype = AA  length = 457
FEATURE                 Location/Qualifiers
source                  1..457
                        mol_type = protein
                        organism = synthetic construct
SEQUENCE: 7
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDSPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 8            moltype = AA  length = 457
FEATURE                 Location/Qualifiers
source                  1..457
                        mol_type = protein
                        organism = synthetic construct
SEQUENCE: 8
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 9            moltype = AA  length = 457
FEATURE                 Location/Qualifiers
source                  1..457
                        mol_type = protein
                        organism = synthetic construct
SEQUENCE: 9
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDVPGGDIGV  180
KAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 10           moltype = AA  length = 457
FEATURE                 Location/Qualifiers
source                  1..457
                        mol_type = protein
                        organism = synthetic construct
SEQUENCE: 10
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDVPGGDIGV  180
RAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 11           moltype = AA  length = 457
FEATURE                 Location/Qualifiers
source                  1..457
                        mol_type = protein
                        organism = synthetic construct
SEQUENCE: 11
```

```
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDVPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 12          moltype = AA  length = 457
FEATURE                Location/Qualifiers
source                 1..457
                       mol_type = protein
                       organism = synthetic construct
SEQUENCE: 12
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDVPGGDIGV  180
GAREVGYLWG QYKRITKANE SGILTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 13          moltype = AA  length = 457
FEATURE                Location/Qualifiers
source                 1..457
                       mol_type = protein
                       organism = synthetic construct
SEQUENCE: 13
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLVGGGKGGS NFNPKGKSDS EIMRFCQAFM TELYRHIGPD VDVPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 14          moltype = AA  length = 457
FEATURE                Location/Qualifiers
source                 1..457
                       mol_type = protein
                       organism = synthetic construct
SEQUENCE: 14
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLIGGGKGGS NFNPKGKSDS EIMRFCQAFM TELYRHIGPD VDSPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 15          moltype = AA  length = 457
FEATURE                Location/Qualifiers
source                 1..457
                       mol_type = protein
                       organism = synthetic construct
SEQUENCE: 15
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLIGGGKGGS NFNPKGKSDS EIMRFCQAFM TELYRHIGPD VDGPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 16          moltype = AA  length = 457
FEATURE                Location/Qualifiers
source                 1..457
                       mol_type = protein
                       organism = synthetic construct
SEQUENCE: 16
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLIGGGKGGS NFNPKGKSDS EIMRFCQAFM TELYRHIGPD VDVPGGDIGV  180
GRREVGYLWG QYKRITKANE SGVLTGKTPG YGGSLARKEA TGYGTVYFVE EMLKEVNDSF  240
```

-continued

EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA ANAGGVAVSA LEMAQDSSRV FWTFEEVDAK LHQIMKNIYA 420
DSKAAADKYG YPGNLVVGAN IAGFIKVADG MLAEGIY 457

SEQ ID NO: 17 moltype = AA length = 457
FEATURE Location/Qualifiers
source 1..457
mol_type = protein
organism = synthetic construct
SEQUENCE: 17
MTTTTVSNDQ LAKEYVDGVF EQLKNQNSHQ AEFLQAAEEI FISLVPVFAQ HPEYIKANIL 60
SRIVEPDRII SFRVAWQDDN NQVQVNRGYR VQYSNVMGPY KGGLRFHPSV NESIIKFLGF 120
EQIFKNALTG QPVGGGKGGS NFNPKGKSDS EIMRFCQAFM TELYRHIGPD VDSPGGDIGV 180
GAREVGYLWG QYKRITKANE SGVLTGKTPG YGGSLARKEA TGYGTVYFVE EMLKEVNDSF 240
EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA ANAGGVAVSA LEMAQDSSRV FWTFEEVDAK LHQIMKNIYA 420
DSKAAADKYG YPGNLVVGAN IAGFIKVADG MLAEGIY 457

SEQ ID NO: 18 moltype = AA length = 457
FEATURE Location/Qualifiers
source 1..457
mol_type = protein
organism = synthetic construct
SEQUENCE: 18
MTTTTVSNDQ LAKEYVDGVF EQLKNQNSHQ AEFLQAAEEI FISLVPVFAQ HPEYIKANIL 60
SRIVEPDRII SFRVAWQDDN NQVQVNRGYR VQYSNVMGPY KGGLRFHPSV NESIIKFLGF 120
EQIFKNALTG QPVGGGKGGS NFNPKGKSDS EIMRFCQAFM TELYRHIGPD VDGPGGDIGV 180
GAREVGYLWG QYKRITKANE SGVLTGKTPG YGGSLARKEA TGYGTVYFVE EMLKEVNDSF 240
EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA ANAGGVAVSA LEMAQDSSRV FWTFEEVDAK LHQIMKNIYA 420
DSKAAADKYG YPGNLVVGAN IAGFIKVADG MLAEGIY 457

SEQ ID NO: 19 moltype = AA length = 457
FEATURE Location/Qualifiers
source 1..457
mol_type = protein
organism = synthetic construct
SEQUENCE: 19
MTTTTVSNDQ LAKEYVDGVF EQLKNQNSHQ AEFLQAAEEI FISLVPVFAQ HPEYIKANIL 60
SRIVEPDRII SFRVAWQDDN NQVQVNRGYR VQYSNVMGPY KGGLRFHPSV NESIIKFLGF 120
EQIFKNALTG QPVGGGKGGS NFNPKGKSDS EIMRFCQAFM TELYRHIGPD VDVPGGDIGV 180
GRREVGYLWG QYKRITKANE SGVLTGKTPG YGGSLARKEA TGYGTVYFVE EMLKEVNDSF 240
EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA ANAGGVAVSA LEMAQDSSRV FWTFEEVDAK LHQIMKNIYA 420
DSKAAADKYG YPGNLVVGAN IAGFIKVADG MLAEGIY 457

SEQ ID NO: 20 moltype = AA length = 457
FEATURE Location/Qualifiers
source 1..457
mol_type = protein
organism = synthetic construct
SEQUENCE: 20
MTTTTVSNDQ LAKEYVDGVF EQLKNQNSHQ AEFLQAAEEI FISLVPVFAQ HPEYIKANIL 60
SRIVEPDRII SFRVAWQDDN NQVQVNRGYR VQYSNVMGPY KGGLRFHPSV NESIIKFLGF 120
EQIFKNALTG QPIGGGKGGS NFNPKGKSDS EIMRFCQAFM TELYRHIGPD VDSPGGDIGV 180
GRREVGYLWG QYKRITKANE SGVLTGKTPG YGGSLARKEA TGYGTVYFVE EMLKEVNDSF 240
EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA ANAGGVAVSA LEMAQDSSRV FWTFEEVDAK LHQIMKNIYA 420
DSKAAADKYG YPGNLVVGAN IAGFIKVADG MLAEGIY 457

SEQ ID NO: 21 moltype = AA length = 457
FEATURE Location/Qualifiers
source 1..457
mol_type = protein
organism = synthetic construct
SEQUENCE: 21
MTTTTVSNDQ LAKEYVDGVF EQLKNQNSHQ AEFLQAAEEI FISLVPVFAQ HPEYIKANIL 60
SRIVEPDRII SFRVAWQDDN NQVQVNRGYR VQYSNVMGPY KGGLRFHPSV NESIIKFLGF 120
EQIFKNALTG QPIGGGKGGS NFNPKGKSDS EIMRFCQAFM TELYRHIGPD VDGPGGDIGV 180
GRREVGYLWG QYKRITKANE SGVLTGKTPG YGGSLARKEA TGYGTVYFVE EMLKEVNDSF 240
EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA ANAGGVAVSA LEMAQDSSRV FWTFEEVDAK LHQIMKNIYA 420
DSKAAADKYG YPGNLVVGAN IAGFIKVADG MLAEGIY 457

```
SEQ ID NO: 22          moltype = AA  length = 457
FEATURE                Location/Qualifiers
source                 1..457
                       mol_type = protein
                       organism = synthetic construct
SEQUENCE: 22
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLVGGGKGGS NFNPKGKSDS EIMRFCQAFM TELYRHIGPD VDSPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                            457

SEQ ID NO: 23          moltype = AA  length = 457
FEATURE                Location/Qualifiers
source                 1..457
                       mol_type = protein
                       organism = synthetic construct
SEQUENCE: 23
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLVGGGKGGS NFNPKGKSDS EIMRFCQAFM TELYRHIGPD VDGPGGDIGV  180
GAREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                            457

SEQ ID NO: 24          moltype = AA  length = 457
FEATURE                Location/Qualifiers
source                 1..457
                       mol_type = protein
                       organism = synthetic construct
SEQUENCE: 24
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLVGGGKGGS NFNPKGKSDS EIMRFCQAFM TELYRHIGPD VDVPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                            457

SEQ ID NO: 25          moltype = AA  length = 457
FEATURE                Location/Qualifiers
source                 1..457
                       mol_type = protein
                       organism = synthetic construct
SEQUENCE: 25
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLIGGGKGGS NFNPKGKSDS EIMRFCQAFM TELYRHIGPD VDSPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                            457

SEQ ID NO: 26          moltype = AA  length = 457
FEATURE                Location/Qualifiers
source                 1..457
                       mol_type = protein
                       organism = synthetic construct
SEQUENCE: 26
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                            457

SEQ ID NO: 27          moltype = AA  length = 457
FEATURE                Location/Qualifiers
source                 1..457
```

```
                        mol_type = protein
                        organism = synthetic construct
SEQUENCE: 27
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPVGGGKGGS NFNPKGKSDS EIMRFCQAFM TELYRHIGPD VDSPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 28           moltype = AA  length = 457
FEATURE                 Location/Qualifiers
source                  1..457
                        mol_type = protein
                        organism = synthetic construct
SEQUENCE: 28
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPVGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 29           moltype = AA  length = 457
FEATURE                 Location/Qualifiers
source                  1..457
                        mol_type = protein
                        organism = synthetic construct
SEQUENCE: 29
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLVGGGKGGS NFNPKGKSDS EIMRFCQAFM TELYRHIGPD VDSPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 30           moltype = AA  length = 457
FEATURE                 Location/Qualifiers
source                  1..457
                        mol_type = protein
                        organism = synthetic construct
SEQUENCE: 30
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QLVGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 31           moltype = AA  length = 457
FEATURE                 Location/Qualifiers
source                  1..457
                        mol_type = protein
                        organism = synthetic construct
SEQUENCE: 31
MTITTVSNEQ LAKEYVDGVF EQLKQQNCHQ AEFLQAAEEI FISLVPVFVQ HPEYIKANIL  60
SRIVEPDRII SFRVAWQDDH NQVQVNRGYR VQYSNVMGPY KGGLRFHPSV NESIIKFLGF  120
EQIFKNALTG QPIGGGKGGS NFDPKGKSDS EIMRFCQAFM TELYRHIGPD VDVPGGDIGV  180
GAREVGYLWG QYKRLTKASE SGVLTGKTPG YGGSLARKEA TGYGTVYFVN EMLKDVNDSF  240
EGKTVVVSGS GNVSTYAIEK AQQYGAKVVA CSDSSGYIYD PEGLDLDVIK EIKEVKGDRI  300
STYVSYRPNA TFTNGCTGIW TIPCDIALPC ATQNEINGES ARTLISNGVK AIGEGANMPS  360
DLEAINEFLN AGVLFGPAKA ANAGGVAVSA LEMAQDSSRV FWSFEEVDAK LHQIMKDIYS  420
DSKAAAEKYG FPGNLVMGAN IAGFIKVADG MLTEGIY                          457

SEQ ID NO: 32           moltype = AA  length = 457
FEATURE                 Location/Qualifiers
source                  1..457
                        mol_type = protein
                        organism = synthetic construct
SEQUENCE: 32
MTITTVSNEQ LAKEYVDGVF EQLKQQNCHQ AEFLQAAEEI FISLVPVFVQ HPEYIKANIL  60
```

-continued

```
SRIVEPDRII SFRVAWQDDH NQVQVNRGYR VQYSNVMGPY KGGLRFHPSV NESIIKFLGF  120
EQIFKNALTG QLIGGGKGGS NFDPKGKSDS EIMRFCQAFM TELYRHIGPD VDVPGGDIGV  180
GAREVGYLWG QYKRLTKASE SGVLTGKTPG YGGSLARKEA TGYGTVYFVN EMLKDVNDSF  240
EGKTVVVSGS GNVSTYAIEK AQQYGAKVVA CSDSSGYIYD PEGLDLDVIK EIKEVKGDRI  300
STYVSYRPNA TFTNGCTGIW TIPCDIALPC ATQNEINGES ARTLISNGVK AIGEGANMPS  360
DLEAINEFLN AGVLFGPAKA ANAGGVAVSA LEMAQDSSRV FWSFEEVDAK LHQIMKDIYS  420
DSKAAAEKYG FPGNLVMGAN IAGFIKVADG MLTEGIY                          457

SEQ ID NO: 33          moltype = AA  length = 457
FEATURE                Location/Qualifiers
source                 1..457
                       mol_type = protein
                       organism = synthetic construct
SEQUENCE: 33
MTITTVSNEQ LAKEYVDGVF EQLKQQNCHQ AEFLQAAEEI FISLVPVFVQ HPEYIKANIL  60
SRIVEPDRII SFRVAWQDDH NQVQVNRGYR VQYSNVMGPY KGGLRFHPSV NESIIKFLGF  120
EQIFKNALTG QLIGGGKGGS NFDPKGKSDS EIMRFCQAFM TELYRHIGPD VDVPGGDIGV  180
GAREVGYLWG QYKRLTKASE SGVLTGKTPG YGGSLARKEA TGYGTVYFVN EMLKDVNDSF  240
EGKTVVVSGS GNVSTYAIEK AQQYGAKVVA CSDSSGYIYD PEGLDLDVIK EIKEVKGDRI  300
STYVSYRPNA TFTNGCTGIW TIPCDIALPC ATQNEINGES ARTLISNGVK AIGEGANMPS  360
DLEAINEFLN AGVLFGPAKA ANAGGVAVSA LEMAQDSSRV FWSFEEVDAK LHQIMKDIYS  420
DSKAAAEKYG FPGNLVMGAN IAGFIKVADG MLTEGIY                          457

SEQ ID NO: 34          moltype = AA  length = 457
FEATURE                Location/Qualifiers
source                 1..457
                       mol_type = protein
                       organism = synthetic construct
SEQUENCE: 34
MTITTVSNEQ LAKEYVDGVF EQLKQQNCHQ AEFLQAAEEI FISLVPVFVQ HPEYIKANIL  60
SRIVEPDRII SFRVAWQDDH NQVQVNRGYR VQYSNVMGPY KGGLRFHPSV NESIIKFLGF  120
EQIFKNALTG QPIGGGKGGS NFDPKGKSDS EIMRFCQAFM TELYRHIGPD VDSPGGDIGV  180
GAREVGYLWG QYKRLTKASE SGVLTGKTPG YGGSLARKEA TGYGTVYFVN EMLKDVNDSF  240
EGKTVVVSGS GNVSTYAIEK AQQYGAKVVA CSDSSGYIYD PEGLDLDVIK EIKEVKGDRI  300
STYVSYRPNA TFTNGCTGIW TIPCDIALPC ATQNEINGES ARTLISNGVK AIGEGANMPS  360
DLEAINEFLN AGVLFGPAKA ANAGGVAVSA LEMAQDSSRV FWSFEEVDAK LHQIMKDIYS  420
DSKAAAEKYG FPGNLVMGAN IAGFIKVADG MLTEGIY                          457

SEQ ID NO: 35          moltype = AA  length = 457
FEATURE                Location/Qualifiers
source                 1..457
                       mol_type = protein
                       organism = synthetic construct
SEQUENCE: 35
MTITTVSNEQ LAKEYVDGVF EQLKQQNCHQ AEFLQAAEEI FISLVPVFVQ HPEYIKANIL  60
SRIVEPDRII SFRVAWQDDH NQVQVNRGYR VQYSNVMGPY KGGLRFHPSV NESIIKFLGF  120
EQIFKNALTG QPIGGGKGGS NFDPKGKSDS EIMRFCQAFM TELYRHIGPD VDGPGGDIGV  180
GAREVGYLWG QYKRLTKASE SGVLTGKTPG YGGSLARKEA TGYGTVYFVN EMLKDVNDSF  240
EGKTVVVSGS GNVSTYAIEK AQQYGAKVVA CSDSSGYIYD PEGLDLDVIK EIKEVKGDRI  300
STYVSYRPNA TFTNGCTGIW TIPCDIALPC ATQNEINGES ARTLISNGVK AIGEGANMPS  360
DLEAINEFLN AGVLFGPAKA ANAGGVAVSA LEMAQDSSRV FWSFEEVDAK LHQIMKDIYS  420
DSKAAAEKYG FPGNLVMGAN IAGFIKVADG MLTEGIY                          457

SEQ ID NO: 36          moltype = AA  length = 457
FEATURE                Location/Qualifiers
source                 1..457
                       mol_type = protein
                       organism = synthetic construct
SEQUENCE: 36
MTITTVSNEQ LAKEYVDGVF EQLKQQNCHQ AEFLQAAEEI FISLVPVFVQ HPEYIKANIL  60
SRIVEPDRII SFRVAWQDDH NQVQVNRGYR VQYSNVMGPY KGGLRFHPSV NESIIKFLGF  120
EQIFKNALTG QPIGGGKGGS NFDPKGKSDS EIMRFCQAFM TELYRHIGPD VDVPGGDIGV  180
GRREVGYLWG QYKRLTKASE SGVLTGKTPG YGGSLARKEA TGYGTVYFVN EMLKDVNDSF  240
EGKTVVVSGS GNVSTYAIEK AQQYGAKVVA CSDSSGYIYD PEGLDLDVIK EIKEVKGDRI  300
STYVSYRPNA TFTNGCTGIW TIPCDIALPC ATQNEINGES ARTLISNGVK AIGEGANMPS  360
DLEAINEFLN AGVLFGPAKA ANAGGVAVSA LEMAQDSSRV FWSFEEVDAK LHQIMKDIYS  420
DSKAAAEKYG FPGNLVMGAN IAGFIKVADG MLTEGIY                          457

SEQ ID NO: 37          moltype = AA  length = 457
FEATURE                Location/Qualifiers
source                 1..457
                       mol_type = protein
                       organism = synthetic construct
SEQUENCE: 37
MTITTVSNEQ LAKEYVDGVF EQLKQQNCHQ AEFLQAAEEI FISLVPVFVQ HPEYIKANIL  60
SRIVEPDRII SFRVAWQDDH NQVQVNRGYR VQYSNVMGPY KGGLRFHPSV NESIIKFLGF  120
EQIFKNALTG QPIGGGKGGS NFDPKGKSDS EIMRFCQAFM TELYRHIGPD VDGPGGDIGV  180
GRREVGYLWG QYKRLTKASE SGVLTGKTPG YGGSLARKEA TGYGTVYFVN EMLKDVNDSF  240
EGKTVVVSGS GNVSTYAIEK AQQYGAKVVA CSDSSGYIYD PEGLDLDVIK EIKEVKGDRI  300
```

-continued

```
STYVSYRPNA TFTNGCTGIW TIPCDIALPC ATQNEINGES ARTLISNGVK AIGEGANMPS  360
DLEAINEFLN AGVLFGPAKA ANAGGVAVSA LEMAQDSSRV FWSFEEVDAK LHQIMKDIYS  420
DSKAAAEKYG FPGNLVMGAN IAGFIKVADG MLTEGIY                           457

SEQ ID NO: 38          moltype = AA  length = 457
FEATURE                Location/Qualifiers
source                 1..457
                       mol_type = protein
                       organism = synthetic construct
SEQUENCE: 38
MTITTVSNEQ LAKEYVDGVF EQLKQQNCHQ AEFLQAAEEI FISLVPVFVQ HPEYIKANIL  60
SRIVEPDRII SFRVAWQDDH NQVQVNRGYR VQYSNVMGPY KGGLRFHPSV NESIIKFLGF  120
EQVFKNALTG QPIGGGKGGS NFDPKGKSDS EIMRFCQAFM TELYRHIGPD VDSPGGDIGV  180
GRREVGYLWG QYKRLTKASE SGVLTGKTPG YGGSLARKEA TGYGTVYFVN EMLKDVNDSF  240
EGKTVVVSGS GNVSTYAIEK AQQYGAKVVA CSDSSGYIYD PEGLDLDVIK EIKEVKGDRI  300
STYVSYRPNA TFTNGCTGIW TIPCDIALPC ATQNEINGES ARTLISNGVK AIGEGANMPS  360
DLEAINEFLN AGVLFGPAKA ANAGGVAVSA LEMAQDSSRV FWSFEEVDAK LHQIMKDIYS  420
DSKAAAEKYG FPGNLVMGAN IAGFIKVADG MLTEGIY                           457

SEQ ID NO: 39          moltype = AA  length = 457
FEATURE                Location/Qualifiers
source                 1..457
                       mol_type = protein
                       organism = synthetic construct
SEQUENCE: 39
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                           457

SEQ ID NO: 40          moltype = AA  length = 457
FEATURE                Location/Qualifiers
source                 1..457
                       mol_type = protein
                       organism = synthetic construct
SEQUENCE: 40
MTTTTVSNDQ LAKEYVDGVF EELKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                           457

SEQ ID NO: 41          moltype = AA  length = 457
FEATURE                Location/Qualifiers
source                 1..457
                       mol_type = protein
                       organism = synthetic construct
SEQUENCE: 41
MTTTTVSNDQ LAKEYVDGVF EQMKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                           457

SEQ ID NO: 42          moltype = AA  length = 457
FEATURE                Location/Qualifiers
source                 1..457
                       mol_type = protein
                       organism = synthetic construct
SEQUENCE: 42
MTTTTVSNDQ LAKEYVDGVF EQLKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                           457
```

```
SEQ ID NO: 43           moltype = AA  length = 457
FEATURE                 Location/Qualifiers
source                  1..457
                        mol_type = protein
                        organism = synthetic construct
SEQUENCE: 43
MTTTTVSNSQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 44           moltype = AA  length = 457
FEATURE                 Location/Qualifiers
source                  1..457
                        mol_type = protein
                        organism = synthetic construct
SEQUENCE: 44
MTTTTVSNLQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 45           moltype = AA  length = 457
FEATURE                 Location/Qualifiers
source                  1..457
                        mol_type = protein
                        organism = synthetic construct
SEQUENCE: 45
MTTTTVSNYQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 46           moltype = AA  length = 457
FEATURE                 Location/Qualifiers
source                  1..457
                        mol_type = protein
                        organism = synthetic construct
SEQUENCE: 46
MTTTTVSNDQ LAKEYVDGVF EQLKDQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 47           moltype = AA  length = 457
FEATURE                 Location/Qualifiers
source                  1..457
                        mol_type = protein
                        organism = synthetic construct
SEQUENCE: 47
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAWE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 48           moltype = AA  length = 457
FEATURE                 Location/Qualifiers
source                  1..457
                        mol_type = protein
```

```
                         organism = synthetic construct
SEQUENCE: 48
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 49            moltype = AA  length = 457
FEATURE                  Location/Qualifiers
source                   1..457
                         mol_type = protein
                         organism = synthetic construct
SEQUENCE: 49
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EGKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 50            moltype = AA  length = 457
FEATURE                  Location/Qualifiers
source                   1..457
                         mol_type = protein
                         organism = synthetic construct
SEQUENCE: 50
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFEPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 51            moltype = AA  length = 457
FEATURE                  Location/Qualifiers
source                   1..457
                         mol_type = protein
                         organism = synthetic construct
SEQUENCE: 51
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQSYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 52            moltype = AA  length = 457
FEATURE                  Location/Qualifiers
source                   1..457
                         mol_type = protein
                         organism = synthetic construct
SEQUENCE: 52
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQKYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 53            moltype = AA  length = 457
FEATURE                  Location/Qualifiers
source                   1..457
                         mol_type = protein
                         organism = synthetic construct
SEQUENCE: 53
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
```

```
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGQA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 54          moltype = AA  length = 457
FEATURE                Location/Qualifiers
source                 1..457
                       mol_type = protein
                       organism = synthetic construct
SEQUENCE: 54
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 55          moltype = AA  length = 457
FEATURE                Location/Qualifiers
source                 1..457
                       mol_type = protein
                       organism = synthetic construct
SEQUENCE: 55
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG SPGNLVVGAN IAGFIKVADG MLAEGIY                          457

SEQ ID NO: 56          moltype = AA  length = 457
FEATURE                Location/Qualifiers
source                 1..457
                       mol_type = protein
                       organism = synthetic construct
SEQUENCE: 56
MTTTTVSNDQ LAKEYVDGVF EQLKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKANE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVKGAN IAGFIKVADG MLAEGIY                          457

SEQ ID NO: 57          moltype = AA  length = 457
FEATURE                Location/Qualifiers
source                 1..457
                       mol_type = protein
                       organism = synthetic construct
SEQUENCE: 57
MTTTTVSNDQ LAKEYVDGVF EQLKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAWE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 58          moltype = AA  length = 457
FEATURE                Location/Qualifiers
source                 1..457
                       mol_type = protein
                       organism = synthetic construct
SEQUENCE: 58
MTTTTVSNDQ LAKEYVDGVF EELKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAWE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
```

-continued

```
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 59          moltype = AA  length = 457
FEATURE                Location/Qualifiers
source                 1..457
                       mol_type = protein
                       organism = synthetic construct
SEQUENCE: 59
MTTTTVSNDQ LAKEYVDGVF EQLKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 60          moltype = AA  length = 457
FEATURE                Location/Qualifiers
source                 1..457
                       mol_type = protein
                       organism = synthetic construct
SEQUENCE: 60
MTTTTVSNDQ LAKEYVDGVF EELKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 61          moltype = AA  length = 457
FEATURE                Location/Qualifiers
source                 1..457
                       mol_type = protein
                       organism = synthetic construct
SEQUENCE: 61
MTTTTVSNDQ LAKEYVDGVF EQLKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 62          moltype = AA  length = 457
FEATURE                Location/Qualifiers
source                 1..457
                       mol_type = protein
                       organism = synthetic construct
SEQUENCE: 62
MTTTTVSNDQ LAKEYVDGVF EELKNQNSHQ AEFLQAAEEI FISLVPVFAQ HPEYIKANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 63          moltype = AA  length = 457
FEATURE                Location/Qualifiers
source                 1..457
                       mol_type = protein
                       organism = synthetic construct
SEQUENCE: 63
MTTTTVSNDQ LAKEYVDGVF EELKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 64          moltype = AA  length = 457
```

```
FEATURE                 Location/Qualifiers
source                  1..457
                        mol_type = protein
                        organism = synthetic construct
SEQUENCE: 64
MTTTTVSNDQ LAKEYVDGVF EELKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAWE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYA  420
DSKAAADKYG YPGNLVVGAN IAGFIKVADG MLAEGIY                          457

SEQ ID NO: 65           moltype = AA  length = 457
FEATURE                 Location/Qualifiers
source                  1..457
                        mol_type = protein
                        organism = synthetic construct
SEQUENCE: 65
MTTTTVSNDQ LAKEYVDGVF EELKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 66           moltype = AA  length = 457
FEATURE                 Location/Qualifiers
source                  1..457
                        mol_type = protein
                        organism = synthetic construct
SEQUENCE: 66
MTTTTVSNDQ LAKEYVDGVF EELKNQNSHQ HEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 67           moltype = AA  length = 457
FEATURE                 Location/Qualifiers
source                  1..457
                        mol_type = protein
                        organism = synthetic construct
SEQUENCE: 67
MTTTTVSNDQ LAKEYVDGVF EELKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQILKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 68           moltype = AA  length = 457
FEATURE                 Location/Qualifiers
source                  1..457
                        mol_type = protein
                        organism = synthetic construct
SEQUENCE: 68
MTTTTVSNDQ LAKEYVDGVF EELKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLGRKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA ANAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 69           moltype = AA  length = 457
FEATURE                 Location/Qualifiers
source                  1..457
                        mol_type = protein
                        organism = synthetic construct
```

-continued

SEQUENCE: 69
MTTTTVSNDQ LAKEYVDGVF EELKNQNSHQ HEFLQAAEEI FISLVPVFAQ HPEYIQANIL 60
SRIVEPDRII SFRVAWQDDN NQVQVNRGYR VQYSNVMGPY KGGLRFHPSV NESIIKFLGF 120
EQILKNALTG QPIGGGKGGS NFNPKGKSDS EIMRFCQAFM TELYRHIGPD VDGPGGDIGV 180
GRREVGYLWG QYKRITKAYE SGVLTGKTPG YGGSLARKEA TGYGTVYFVE EMLKEVNDSF 240
EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA ANAGGVAVSA LEMAQDSSRV FWTFEEVDAK LHQIMKNIYR 420
DSKAAADKYG YPGNLVVGAN IAGFIKVADG MLAEGIY 457

SEQ ID NO: 70 moltype = AA length = 457
FEATURE Location/Qualifiers
source 1..457
mol_type = protein
organism = synthetic construct
SEQUENCE: 70
MTTTTVSNDQ LAKEYVDGVF EELKNQNSHQ HEFLQAAEEI FISLVPVFAQ HPEYIQANIL 60
SRIVEPDRII SFRVAWQDDN NQVQVNRGYR VQYSNVMGPY KGGLRFHPSV NESIIKFLGF 120
EQIFKNALTG QPIGGGKGGS NFNPKGKSDS EIMRFCQAFM TELYRHIGPD VDGPGGDIGV 180
GRREVGYLWG QYKRITKAYE SGVLTGKTPG YGGSLGRKEA TGYGTVYFVE EMLKEVNDSF 240
EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA ANAGGVAVSA LEMAQDSSRV FWTFEEVDAK LHQIMKNIYR 420
DSKAAADKYG YPGNLVVGAN IAGFIKVADG MLAEGIY 457

SEQ ID NO: 71 moltype = AA length = 457
FEATURE Location/Qualifiers
source 1..457
mol_type = protein
organism = synthetic construct
SEQUENCE: 71
MTTTTVSNDQ LAKEYVDGVF EELKNQNSHQ AEFLQAAEEI FISLVPVFAQ HPEYIQANIL 60
SRIVEPDRII SFRVAWQDDN NQVQVNRGYR VQYSNVMGPY KGGLRFHPSV NESIIKFLGF 120
EQILKNALTG QPIGGGKGGS NFNPKGKSDS EIMRFCQAFM TELYRHIGPD VDGPGGDIGV 180
GRREVGYLWG QYKRITKAYE SGVLTGKTPG YGGSLGRKEA TGYGTVYFVE EMLKEVNDSF 240
EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA ANAGGVAVSA LEMAQDSSRV FWTFEEVDAK LHQIMKNIYR 420
DSKAAADKYG YPGNLVVGAN IAGFIKVADG MLAEGIY 457

SEQ ID NO: 72 moltype = AA length = 457
FEATURE Location/Qualifiers
source 1..457
mol_type = protein
organism = synthetic construct
SEQUENCE: 72
MTTTTVSNDQ LAKEYVDGVF EELKNQNSHQ HEFLQAAEEI FISLVPVFAQ HPEYIQANIL 60
SRIVEPDRII SFRVAWQDDN NQVQVNRGYR VQYSNVMGPY KGGLRFHPSV NESIIKFLGF 120
EQILKNALTG QPIGGGKGGS NFNPKGKSDS EIMRFCQAFM TELYRHIGPD VDGPGGDIGV 180
GRREVGYLWG QYKRITKAYE SGVLTGKTPG YGGSLGRKEA TGYGTVYFVE EMLKEVNDSF 240
EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA ANAGGVAVSA LEMAQDSSRV FWTFEEVDAK LHQIMKNIYR 420
DSKAAADKYG YPGNLVVGAN IAGFIKVADG MLAEGIY 457

SEQ ID NO: 73 moltype = AA length = 457
FEATURE Location/Qualifiers
source 1..457
mol_type = protein
organism = synthetic construct
SEQUENCE: 73
MTTTTVSNDQ LAKEYVDGVF EELKNQNSHQ AEFLQAAEEI FISLVPVFAQ HPEYIQANIL 60
SRIVEPDRII SFRVAWQDDN NQVQVNRGYR VQYSNVMGPY KGGLRFHPSV NESIIKFLGF 120
EQIFKNALTG QPIGGGKGGS NFNPKGKSDS EIMRFCQAFM TELYRHIGPD VDGPGGDIGV 180
GRREVGYLWG QYKRITKAYE SGVLTGKTPG YGGSLARKEA TGYGTVYFVE EMLKEVNDSF 240
EDKTVVVSGS GNVSTYAIEK AQAYGAKVVA CSDSSGYIYD AEGLDLDVIK EIKEVKGDRI 300
STYVDYRPNA TFTEGCTGIW SIPCDIALPC ATQNEINGDA ARTLISNGVK AIGEGANMPS 360
DLEAINEFLN AGVLFGPAKA CNAGGVAVSA LEMAQDSSRV FWTFEEVDAK LHQIMKNIYR 420
DSKAAADKYG YPGNLVVGAN IAGFIKVADG MLAEGIY 457

SEQ ID NO: 74 moltype = AA length = 457
FEATURE Location/Qualifiers
source 1..457
mol_type = protein
organism = synthetic construct
SEQUENCE: 74
MTTTTVSNDQ LAKEYVDGVF EELKNQNSHQ HEFLQAAEEI FISLVPVFAQ HPEYIQANIL 60
SRIVEPDRII SFRVAWQDDN NQVQVNRGYR VQYSNVMGPY KGGLRFHPSV NESIIKFLGF 120
EQIFKNALTG QPIGGGKGGS NFNPKGKSDS EIMRFCQAFM TELYRHIGPD VDGPGGDIGV 180

```
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA CNAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 75          moltype = AA  length = 457
FEATURE                Location/Qualifiers
source                 1..457
                       mol_type = protein
                       organism = synthetic construct
SEQUENCE: 75
MTTTTVSNDQ LAKEYVDGVF EELKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQILKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA CNAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 76          moltype = AA  length = 457
FEATURE                Location/Qualifiers
source                 1..457
                       mol_type = protein
                       organism = synthetic construct
SEQUENCE: 76
MTTTTVSNDQ LAKEYVDGVF EELKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLGRKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA CNAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 77          moltype = AA  length = 457
FEATURE                Location/Qualifiers
source                 1..457
                       mol_type = protein
                       organism = synthetic construct
SEQUENCE: 77
MTTTTVSNDQ LAKEYVDGVF EELKNQNSHQ HEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQILKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLARKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA CNAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 78          moltype = AA  length = 457
FEATURE                Location/Qualifiers
source                 1..457
                       mol_type = protein
                       organism = synthetic construct
SEQUENCE: 78
MTTTTVSNDQ LAKEYVDGVF EELKNQNSHQ HEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQIFKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLGRKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA CNAGGVAVSA LEMAQDSSRV FWTFEEVDAK LHQIMKNIYR  420
DSKAAADKYG YPGNLVVGAN IAGFIKVADG MLAEGIY                          457

SEQ ID NO: 79          moltype = AA  length = 457
FEATURE                Location/Qualifiers
source                 1..457
                       mol_type = protein
                       organism = synthetic construct
SEQUENCE: 79
MTTTTVSNDQ LAKEYVDGVF EELKNQNSHQ AEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQILKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLGRKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA CNAGGVAVSA LEMAQDSSRV FWTFEEVDAK LHQIMKNIYR  420
```

-continued

```
DSKAAADKYG YPGNLVVGAN IAGFIKVADG MLAEGIY                      457

SEQ ID NO: 80          moltype = AA  length = 457
FEATURE                Location/Qualifiers
source                 1..457
                       mol_type = protein
                       organism = synthetic construct
SEQUENCE: 80
MTTTTVSNDQ LAKEYVDGVF EELKNQNSHQ HEFLQAAEEI FISLVPVFAQ HPEYIQANIL  60
SRIVEPDRII SFRVAWQDDN NQVQVNRGYR VQYSNVMGPY KGGLRFHPSV NESIIKFLGF  120
EQILKNALTG QPIGGGKGGS NFNPKGKSDS EIMRFCQAFM TELYRHIGPD VDGPGGDIGV  180
GRREVGYLWG QYKRITKAYE SGVLTGKTPG YGGSLGRKEA TGYGTVYFVE EMLKEVNDSF  240
EDKTVVVSGS GNVSTYAIEK AQAYGAKVVA CSDSSGYIYD AEGLDLDVIK EIKEVKGDRI  300
STYVDYRPNA TFTEGCTGIW SIPCDIALPC ATQNEINGDA ARTLISNGVK AIGEGANMPS  360
DLEAINEFLN AGVLFGPAKA CNAGGVAVSA LEMAQDSSRV FWTFEEVDAK LHQIMKNIYR  420
DSKAAADKYG YPGNLVVGAN IAGFIKVADG MLAEGIY                      457
```

MODIFIED GLUTAMATE DEHYDROGENASE AND APPLICATION THEREOF

CROSS-REFERENCES TO RELATED APPLICATIONS

This application is a U.S. Nat'l Phase of Int'l Appl. No. PCT/CN2022/143241, filed Dec. 29, 2022, which claims the benefit of priority to Int'l Appl. No. CN 202111670071.9, filed Dec. 31, 2021, and all of which are hereby incorporated herein by reference in their entireties.

SEQUENCE LISTING DISCLOSURE

The contents of the electronic sequence listing (11584980053001.xml; Size: 106,283 bytes; and Date of Creation: Jul. 23, 2026) is herein incorporated by reference in its entirety.

TECHNICAL FIELD

The present invention relates to the field of enzyme engineering. In particular, the present invention refers to a modified glutamate dehydrogenase (GluDH) and the use thereof in the production of glufosinate.

BACKGROUND

Glufosinate (also referred to as 4-[Hydroxy(methyl) phosphono]-D,L-homoalanine) is a herbicide in the second place in the world sales ranking, to which the transgenic crops are tolerant. Glufosinate is a broad-spectrum contact-killing herbicide that results in a disturbance in nitrogen metabolism in a plant by inhibiting the activity of L-glutamine synthetase, and finally kills the plant. Glufosinate has significant advantages over glyphosate, such as the broad application, rapid effect, long duration, low toxicity, safety, etc. Therefore, the sales of glufosinate are increasing quickly, and there will be a great need thereof in the next period, and an excellent prospect.

However, the process for producing glufosinate is complex, resulting in a high difficulty in the production. The high price prevents it from rapidly replacing glyphosate. Currently, the commercial glufosinate is a racemic mixture comprising equal amounts of two optical isomers (D,L-glufosinate), in which only L-glufosinate is biologically active. Therefore, the preparation of chiral pure L-glufosinate by deracemization of D,L-glufosinate is practically important and becomes popular in the synthesis of L-glufosinate in recent years.

In recent years, many methods have been reported for preparing L-glufosinate from D,L-glufosinate. The traditional resolution method by chemical modification is not competitive due to the high cost and the fact that D-glufosinate cannot be used. Currently, the prime and representative technical routes for converting D-glufosinate-ammonium into L-glufosinate, which have been reported, are as follows.

D,L-glufosinate is converted into N-acetyl glufosinate, and then, L-glufosinate is obtained by the selective hydrolysis of L-N-acetyl glufosinate, which is catalyzed by carboxypeptidase, while D-N-Acetyl glufosinate cannot be hydrolyzed, and can be recycled into the hydrolysis step after chemical or enzymatic racemization (see, e.g., CN108690854A). The drawbacks of this method include the multiple steps of reactions, and the need of the separation of L-glufosinate, which is obtained from the hydrolysis, from the N-acetylated substrate.

D-Glufosinate is oxidized into 2-carbonyl-4-(hydroxymethylphosphono) butyric acid (PPO), and then, PPO is reduced or transaminated to generate L-Glufosinate-ammonium. In most of the references, D-amino acid oxidase (DAAO) is used to catalyze the oxidation of D-glufosinate into PPO. PPO can be reduced by formic acid under the catalysis of palladium on carbon to generate D,L-glufosinate, so that D,L-glufosinate can be gradually converted into L-glufosinate due to the stereoselectivity of DAAO (see, e.g., CN105567780A). The drawbacks of this solution include that a great amount of palladium-carbon catalyst is needed, and the raw materials for the reaction (such as oxygen and ammonium formate) will be wasted.

PPO can also be converted into L-glufosinate by the stereoselective transamination reaction catalyzed by L-amino acid transaminase (L-TA) (see, e.g., US20180030487A1). This solution has a drawback that the transamination step is a balanced reaction, and thus, it is needed to provide an excess amount of amino donor (amino acid or organic amine) to achieve a high conversion rate (for example, a conversion rate of 90% when providing 3 equivalents of the amino donor), and the excess amount of amino donor and the corresponding by-products will seriously influence the subsequent separation and purification steps.

In addition, PPO can be converted into L-glufosinate via the stereoselective reduction reaction catalyzed by L-amino acid dehydrogenase (L-AADH) with inorganic ammonium salts as the amino donor with the aid of NAD (P) H cycle consuming formate, glucose or simple alcohols. The reaction catalyzed by L-AADH does not need much excessive hydrogen donor, and can achieve a high conversion rate.

It is reported to utilize the native or modified glutamate dehydrogenase (GluDH) for catalyzing the asymmetric reductive amination of PPO to prepare L-glufosinate (see, e.g., CN107630052B, CN106978453B, CN108588045B and CN109609474A).

However, it is still needed in the art to provide a GluDH having an increased activity for catalyzing the reaction of PPO with an amino donor to generate L-glufosinate and/or having an improved dynamic property (e.g., an increased Vmax value, a decreased Km value or an increased Vmax/Km).

SUMMARY OF THE INVENTION

In the first aspect, the present invention provides a modified glutamate dehydrogenase comprising substitutions of amino acids at two or more positions as compared to the initial GluDH, wherein the modified GluDH has an increased activity for catalyzing the reaction of PPO with an amino donor to generate L-glufosinate, and/or has an improved dynamic property (e.g., an increased Vmax, a decreased Km or an increased Vmax/Km).

In some embodiments, the modified GluDH comprises, as compared to the initial GluDH, a combination of substitutions of amino acids selected from:

the amino acid at position 104 is substituted with C, and the amino acid at position 175 is substituted with G;

the amino acid at position 132 is substituted with L, and the amino acid at position 175 is substituted with G;

the amino acid at position 133 is substituted with V, and the amino acid at position 175 is substituted with G;

the amino acid at position 173 is substituted with G or S, and the amino acid at position 175 is substituted with G;

the amino acid at position 175 is substituted with G, and the amino acid at position 181 is substituted with K or R;

the amino acid at position 175 is substituted with G, and the amino acid at position 182 is substituted with R;

the amino acid at position 175 is substituted with G, and the amino acid at position 203 is substituted with I;

the amino acid at position 132 is substituted with L, the amino acid at position 133 is substituted with V, and the amino acid at position 175 is substituted with G;

the amino acid at position 132 is substituted with L, the amino acid at position 173 is substituted with S, and the amino acid at position 175 is substituted with G;

the amino acid at position 132 is substituted with L, the amino acid at position 175 is substituted with G, and the amino acid at position 182 is substituted with R;

the amino acid at position 133 is substituted with V, the amino acid at position 173 is substituted with G or S, and the amino acid at position 175 is substituted with G;

the amino acid at position 133 is substituted with V, the amino acid at position 175 is substituted with G, and the amino acid at position 182 is substituted with R;

the amino acid at position 173 is substituted with G, the amino acid at position 175 is substituted with G, and the amino acid at position 182 is substituted with R;

the amino acid at position 132 is substituted with L, the amino acid at position 133 is substituted with V, the amino acid at position 173 is substituted with S, and the amino acid at position 175 is substituted with G;

the amino acid at position 132 is substituted with L, the amino acid at position 133 is substituted with V, the amino acid at position 175 is substituted with G, and the amino acid at position 182 is substituted with R;

the amino acid at position 132 is substituted with L, the amino acid at position 173 is substituted with S, the amino acid at position 175 is substituted with G, and the amino acid at position 182 is substituted with R;

the amino acid at position 133 is substituted with V, the amino acid at position 173 is substituted with G or S, the amino acid at position 175 is substituted with G, and the amino acid at position 182 is substituted with R; and the amino acid at position 132 is substituted with L, the amino acid at position 133 is substituted with V, the amino acid at position 173 is substituted with G or S, the amino acid at position 175 is substituted with G, and the amino acid at position 182 is substituted with R, wherein the positions are numbered by reference to SEQ ID NO: 1.

In some embodiments, the modified GluDH comprises substitutions at positions 173, 175 and 182 as compared to the initial GluDH thereof, wherein the positions are numbered by reference to SEQ ID NO: 1. In some embodiments, the amino acid at position 173 is substituted with G. Preferably, the amino acid at position 175 is substituted with G. Preferably, the amino acid at position 182 is substituted with R. In some embodiments, the modified GluDH further comprises substitutions of amino acids at one or more positions selected from positions 9, 22, 23, 25, 31, 56, 124, 143, 199, 216, 242, 263, 339, 420, 431 and 437. Preferably, the amino acid at position 9 is substituted with S, L or Y. Preferably, the amino acid at position 22 is substituted with W or E. Preferably, the amino acid at position 23 is substituted with M. Preferably, the amino acid at position 25 is substituted with D. Preferably, the amino acid at position 31 is substituted with H. Preferably, the amino acid at position 56 is substituted with Q. Preferably, the amino acid at position 124 is substituted with L. Preferably, the amino acid at position 143 is substituted with E. Preferably, the amino acid at position 199 is substituted with W or Y. Preferably, the amino acid at position 216 is substituted with G. Preferably, the amino acid at position 263 is substituted with S. Preferably, the amino acid at position 339 is substituted with Q. Preferably, the amino acid at position 420 is substituted with R. Preferably, the amino acid at position 431 is substituted with S. Preferably, the amino acid at position 437 is substituted with K.

In some embodiments, the modified GluDH comprises substitutions of amino acids at positions 22, 56, 173, 175, 182, 199 and 420. Preferably, the amino acid at position 22 is substituted with E. Preferably, the amino acid at position 56 is substituted with Q. Preferably, the amino acid at position 173 is substituted with G. Preferably, the amino acid at position 175 is substituted with G. Preferably, the amino acid at position 182 is substituted with R. Preferably, the amino acid at position 199 is substituted with Y. Preferably, the amino acid at position 420 is substituted with R. In some embodiments, the modified GluDH further comprises substitutions of amino acids at one or more positions selected from positions 31, 124 and 216. Preferably, the amino acid at position 31 is substituted with H. Preferably, the amino acid at position 124 is substituted with L. Preferably, the amino acid at position 216 is substituted with G.

In some embodiments, the initial GluDH is a wildtype GluDH. In some embodiments, the initial GluDH is derived from a microorganism of Bacillaceae, preferably a microorganism of *Lysinibacillus* or *Bacillus*, more preferably *Lysinibacillus sphaericus* or *Bacillus* velezensis. In a preferred embodiment, the initial GluDH comprises an amino acid sequence of SEQ ID NO: 1 or 2.

In some embodiments, the modified GluDH comprises an amino acid sequence of one of SEQ ID NOs: 4-14, 16-19, 21, 22, 24, 25, 27-30, 32-48, 50, 51 and 53-72.

The present invention further provides a modified GluDH comprising, as compared to the initial GluDH, substitutions of amino acids at positions 22, 56, 173, 175, 182, 199, 381 and 420, wherein the amino acid at position 22 is substituted with E, the amino acid at position 56 is substituted with Q, the amino acid at position 173 is substituted with G, the amino acid at position 175 is substituted with G, the amino acid at position 182 is substituted with R, the amino acid at position 199 is substituted with Y, the amino acid at position 381 is substituted with C, the amino acid at position 420 is substituted with R, wherein the positions are numbered by reference to SEQ ID NO: 1, and wherein the modified GluDH, as compared to the initial GluDH, has an increased activity for catalyzing the reaction of 2-carbonyl-4-(hydroxymethylphosphono) butyric acid (PPO) with an amino donor to generate L-glufosinate, and/or has an improved stability, and/or has an increased Vmax, a decreased Km or an increased Vmax/Km.

In some embodiments, the initial GluDH is a wildtype GluDH. In some embodiments, the initial GluDH is derived from a microorganism of Bacillaceae, preferably a microorganism of *Lysinibacillus* or *Bacillus*, more preferably *Lysinibacillus sphaericus* or *Bacillus* velezensis. In some embodiment, the initial GluDH comprises an amino acid sequence of SEQ ID NO: 1 or 2.

In some embodiments, the modified GluDH further comprises substitutions of amino acids at one or more positions selected from positions 31, 124 and 216, wherein the amino acid at position 31 is substituted with H, the amino acid at position 124 is substituted with L, the amino acid at position 216 is substituted with G.

In some embodiments, the modified GluDH further comprises substitutions of amino acids at one or more positions selected from positions 9, 23, 25, 143, 263, 339, 431 and 437, wherein the amino acid at position 9 is substituted with S, L or Y, the amino acid at position 23 is substituted with M, the amino acid at position 25 is substituted with D, the amino acid at position 143 is substituted with E, the amino acid at position 263 is substituted with S, the amino acid at position 339 is substituted with Q, the amino acid at position 431 is substituted with S, the amino acid at position 437 is substituted with K.

In some embodiments, the modified GluDH comprises an amino acid sequence of one of SEQ ID NOs: 73-80.

In some embodiments, the activity of the modified GluDH for catalyzing the reaction of PPO and an amino donor to generate L-glufosinate is at least 100%, 105%, 110%, 120%, 130%, 140%, 150%, 160%, 170%, 180%, 190%, 200% or more of the activity of SEQ ID NO: 3 for catalyzing the reaction.

In the second aspect, the present invention provides a polynucleotide encoding the modified GluDH of the present invention, and a vector comprising the polynucleotide of the present invention.

In the third aspect, the present invention provides a host cell comprising the modified GluDH of the present invention, the coding polynucleotide thereof or the vector comprising the polynucleotide.

In the fourth aspect, the present invention provides a method of producing L-glufosinate comprising contacting the modified GluDH of the present invention or the host cell of the present invention with PPO.

DETAILED DESCRIPTION OF THE INVENTION

The present invention mainly refers to a modified GluDH for catalyzing the reaction of PPO with an amino donor to generate L-glufosinate. Unless otherwise specified, the terms used herein have the meaning generally understood by those skilled in the art.

I. Modified Glutamate Dehydrogenase

As used herein, the terms "glutamate dehydrogenase" and "GluDH" refer to an enzyme catalyzing the dehydrogenation of glutamate to generate α-ketoglutarate. Moreover, GluDH has the activity of catalyzing the reaction of PPO with an amino donor to generate L-glufosinate. The present invention provides modified GluDH polypeptides having an increased activity for catalyzing the reaction of PPO with an amino donor to generate L-glufosinate and/or having an improved dynamic property, including but not limited to an increased Vmax value, a decreased Km value or an increased Vmax/Km.

As used herein, the term "peptide" means a chain comprising at least two amino acids linked by peptide bond. The term "polypeptide" can be exchanged with "protein", and means a chain comprising ten or more amino acid residues. The chemical formulas or sequences of all the peptides and polypeptide herein are written in left-to-right order, showing the direction from the amino terminal to the carboxyl terminal.

The term "amino acid" includes amino acids naturally occurred in proteins and the unnatural amino acids. The conventional nomenclature (one-letter and three-letter) of the amino acids naturally occurred in proteins is employed, which can be seen in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989).

| Amino acid | One-letter | Three-letter |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As used herein, the term "modification" refers to any modification to the polypeptide, for example, the substitution, deletion, insertion and/or addition of amino acid(s).

In some embodiments, the modified GluDH of the present invention comprises the substitutions of amino acids at two or more positions as compared to the initial GluDH thereof, wherein the modified GluDH has an increased activity for catalyzing the reaction of PPO with an amino donor to generate L-glufosinate and/or has an improved dynamic property, including but not limited to an increased Vmax value, a decreased Km value or an increased Vmax/Km.

In some embodiments, the modified GluDH, as compared to the initial GluDH thereof, has the following combinations of substitutions of amino acids:

- the amino acid at position 104 is substituted with C, and the amino acid at position 175 is substituted with G;
- the amino acid at position 132 is substituted with L, and the amino acid at position 175 is substituted with G;
- the amino acid at position 133 is substituted with V, and the amino acid at position 175 is substituted with G;
- the amino acid at position 173 is substituted with G or S, and the amino acid at position 175 is substituted with G;
- the amino acid at position 175 is substituted with G, and the amino acid at position 181 is substituted with K or R;
- the amino acid at position 175 is substituted with G, and the amino acid at position 182 is substituted with R;
- the amino acid at position 175 is substituted with G, and the amino acid at position 203 is substituted with I;
- the amino acid at position 132 is substituted with L, the amino acid at position 133 is substituted with V, and the amino acid at position 175 is substituted with G;

the amino acid at position 132 is substituted with L, the amino acid at position 173 is substituted with S, and the amino acid at position 175 is substituted with G;

the amino acid at position 132 is substituted with L, the amino acid at position 175 is substituted with G, and the amino acid at position 182 is substituted with R;

the amino acid at position 133 is substituted with V, the amino acid at position 173 is substituted with G or S, and the amino acid at position 175 is substituted with G;

the amino acid at position 133 is substituted with V, the amino acid at position 175 is substituted with G, and the amino acid at position 182 is substituted with R;

the amino acid at position 173 is substituted with G, the amino acid at position 175 is substituted with G, and the amino acid at position 182 is substituted with R;

the amino acid at position 132 is substituted with L, the amino acid at position 133 is substituted with V, the amino acid at position 173 is substituted with S, and the amino acid at position 175 is substituted with G;

the amino acid at position 132 is substituted with L, the amino acid at position 133 is substituted with V, the amino acid at position 175 is substituted with G, and the amino acid at position 182 is substituted with R;

the amino acid at position 132 is substituted with L, the amino acid at position 173 is substituted with S, the amino acid at position 175 is substituted with G, and the amino acid at position 182 is substituted with R;

the amino acid at position 133 is substituted with V, the amino acid at position 173 is substituted with G or S, the amino acid at position 175 is substituted with G, and the amino acid at position 182 is substituted with R; and the amino acid at position 132 is substituted with L, the amino acid at position 133 is substituted with V, the amino acid at position 173 is substituted with G or S, the amino acid at position 175 is substituted with G, and the amino acid at position 182 is substituted with R, wherein the positions are numbered by reference to SEQ ID NO: 1.

In some embodiments, the modified GluDH of the present invention comprises substitutions at positions 132 and 175 as compared to the initial GluDH thereof, wherein the positions are numbered by reference to SEQ ID NO: 1. Preferably, the amino acid at position 132 is substituted with L, and the amino acid at position 175 is substituted with G. In some embodiments, the modified GluDH of the present invention further comprises substitutions at one or more positions selected from positions 104, 133, 173, 181 and 182 as compared to the initial GluDH thereof. In some embodiments, the amino acid at position 104 is substituted with C. In some embodiments, the amino acid at position 133 is substituted with V. In some embodiments, the amino acid at position 173 is substituted with G or S. In some embodiments, the amino acid at position 181 is substituted with K or R. In some embodiments, the amino acid at position 182 is substituted with R.

In some embodiments, the modified GluDH of the present invention comprises substitutions at positions 133 and 175 as compared to the initial GluDH thereof, wherein the positions are numbered by reference to SEQ ID NO: 1. Preferably, the amino acid at position 133 is substituted with V, and the amino acid at position 175 is substituted with G. In some embodiments, the modified GluDH of the present invention further comprises substitutions at one or more positions selected from positions 104, 132, 173, 181 and 182 as compared to the initial GluDH thereof. In some embodiments, the amino acid at position 104 is substituted with C. In some embodiments, the amino acid at position 132 is substituted with L. In some embodiments, the amino acid at position 173 is substituted with G or S. In some embodiments, the amino acid at position 181 is substituted with K or R. In some embodiments, the amino acid at position 182 is substituted with R.

In some embodiments, the modified GluDH of the present invention comprises substitutions at positions 173 and 175 as compared to the initial GluDH thereof, wherein the positions are numbered by reference to SEQ ID NO: 1. Preferably, the amino acid at position 173 is substituted with G or S, and the amino acid at position 175 is substituted with G. In some embodiments, the modified GluDH of the present invention further comprises substitutions at one or more positions selected from positions 104, 132, 133, 181 and 182 as compared to the initial GluDH thereof. In some embodiments, the amino acid at position 104 is substituted with C. In some embodiments, the amino acid at position 132 is substituted with L. In some embodiments, the amino acid at position 133 is substituted with V. In some embodiments, the amino acid at position 181 is substituted with K or R. In some embodiments, the amino acid at position 182 is substituted with R.

In some embodiments, the modified GluDH of the present invention comprises substitutions at positions 175 and 182 as compared to the initial GluDH thereof, wherein the positions are numbered by reference to SEQ ID NO: 1. Preferably, the amino acid at position 175 is substituted with G, and the amino acid at position 182 is substituted with R. In some embodiments, the modified GluDH of the present invention further comprises substitutions at one or more positions selected from positions 104, 132, 133, 173 and 181 as compared to the initial GluDH thereof. In some embodiments, the amino acid at position 104 is substituted with C. In some embodiments, the amino acid at position 132 is substituted with L. In some embodiments, the amino acid at position 133 is substituted with V. In some embodiments, the amino acid at position 173 is substituted with G or S. In some embodiments, the amino acid at position 181 is substituted with K or R.

In some embodiments, the modified GluDH of the present invention comprises substitutions at positions 132, 133 and 175 as compared to the initial GluDH thereof, wherein the positions are numbered by reference to SEQ ID NO: 1. Preferably, the amino acid at position 132 is substituted with L, the amino acid at position 133 is substituted with V, and the amino acid at position 175 is substituted with G. In some embodiments, the modified GluDH of the present invention further comprises substitutions at one or more positions selected from positions 104, 173, 181 and 182 as compared to the initial GluDH thereof. In some embodiments, the amino acid at position 104 is substituted with C. In some embodiments, the amino acid at position 173 is substituted with G or S. In some embodiments, the amino acid at position 181 is substituted with K or R. In some embodiments, the amino acid at position 182 is substituted with R.

In some embodiments, the modified GluDH of the present invention comprises substitutions at positions 132, 173 and 175 as compared to the initial GluDH thereof, wherein the positions are numbered by reference to SEQ ID NO: 1. Preferably, the amino acid at position 132 is substituted with L, the amino acid at position 173 is substituted with G or S, and the amino acid at position 175 is substituted with G. In some embodiments, the modified GluDH of the present invention further comprises substitutions at one or more positions selected from positions 104, 133, 181 and 182 as compared to the initial GluDH thereof. In some embodiments, the amino acid at position 104 is substituted with C. In some embodiments, the amino acid at position 133 is substituted with V. In some embodiments, the amino acid at position 181 is substituted with K or R. In some embodiments, the amino acid at position 182 is substituted with R.

In some embodiments, the modified GluDH of the present invention comprises substitutions at positions 133, 173 and 175 as compared to the initial GluDH thereof, wherein the positions are numbered by reference to SEQ ID NO: 1. Preferably, the amino acid at position 133 is substituted with V, the amino acid at position 173 is substituted with G or S, and the amino acid at position 175 is substituted with G. In some embodiments, the modified GluDH of the present invention further comprises substitutions at one or more positions selected from positions 104, 132, 181 and 182 as compared to the initial GluDH thereof. In some embodiments, the amino acid at position 104 is substituted with C. In some embodiments, the amino acid at position 132 is substituted with L. In some embodiments, the amino acid at position 181 is substituted with K or R. In some embodiments, the amino acid at position 182 is substituted with R.

In some embodiments, the modified GluDH of the present invention comprises substitutions at positions 132, 175 and 182 as compared to the initial GluDH thereof, wherein the positions are numbered by reference to SEQ ID NO: 1. Preferably, the amino acid at position 132 is substituted with L, the amino acid at position 175 is substituted with G, and the amino acid at position 182 is substituted with R. In some embodiments, the modified GluDH of the present invention further comprises substitutions at one or more positions selected from positions 104, 133, 173 and 181 as compared to the initial GluDH thereof. In some embodiments, the amino acid at position 104 is substituted with C. In some embodiments, the amino acid at position 133 is substituted with V. In some embodiments, the amino acid at position 173 is substituted with G or S. In some embodiments, the amino acid at position 181 is substituted with K or R.

In some embodiments, the modified GluDH of the present invention comprises substitutions at positions 133, 175 and 182 as compared to the initial GluDH thereof, wherein the positions are numbered by reference to SEQ ID NO: 1. Preferably, the amino acid at position 133 is substituted with V, the amino acid at position 175 is substituted with G, and the amino acid at position 182 is substituted with R. In some embodiments, the modified GluDH of the present invention further comprises substitutions at one or more positions selected from positions 104, 132, 173 and 181 as compared to the initial GluDH thereof. In some embodiments, the amino acid at position 104 is substituted with C. In some embodiments, the amino acid at position 132 is substituted with L. In some embodiments, the amino acid at position 173 is substituted with G or S. In some embodiments, the amino acid at position 181 is substituted with K or R.

In some embodiments, the modified GluDH of the present invention comprises substitutions at positions 173, 175 and 182 as compared to the initial GluDH thereof, wherein the positions are numbered by reference to SEQ ID NO: 1. Preferably, the amino acid at position 173 is substituted with G or S, the amino acid at position 175 is substituted with G, and the amino acid at position 182 is substituted with R. In some embodiments, the modified GluDH of the present invention further comprises substitutions at one or more positions selected from positions 104, 132, 133 and 181 as compared to the initial GluDH thereof. In some embodiments, the amino acid at position 104 is substituted with C. In some embodiments, the amino acid at position 132 is substituted with L. In some embodiments, the amino acid at position 133 is substituted with V. In some embodiments, the amino acid at position 181 is substituted with K or R.

In some embodiments, the modified GluDH of the present invention comprises, as compared to the initial GluDH, substitutions of amino acids at positions 22, 56, 173, 175, 182, 199, 381 and 420, wherein the positions are numbered by reference to SEQ ID NO: 1, and wherein the modified GluDH, as compared to the initial GluDH, has an increased activity for catalyzing the reaction of 2-carbonyl-4-(hydroxymethylphosphono) butyric acid (PPO) with an amino donor to generate L-glufosinate, and/or has an improved stability, and/or has an increased Vmax, a decreased Km or an increased Vmax/Km. Preferably, the amino acid at position 22 is substituted with E. Preferably, the amino acid at position 56 is substituted with Q. Preferably, the amino acid at position 173 is substituted with G. Preferably, the amino acid at position 175 is substituted with G. Preferably, the amino acid at position 182 is substituted with R. Preferably, the amino acid at position 199 is substituted with Y. Preferably, the amino acid at position 381 is substituted with C. Preferably, the amino acid at position 420 is substituted with R. In some embodiments, the modified GluDH further comprises substitutions of amino acids at one or more positions selected from positions 31, 124 and 216. Preferably, the amino acid at position 31 is substituted with H. Preferably, the amino acid at position 124 is substituted with L. Preferably, the amino acid at position 216 is substituted with G.

In some embodiments, the modified GluDH of the present invention comprises, as compared to the initial GluDH, substitutions of amino acids:

22E-56Q-173G-175G-182R-199Y-381C-420R;
22E-31H-56Q-173G-175G-182R-199Y-381C-420R;
22E-56Q-124L-173G-175G-182R-199Y-381C-420R;
22E-56Q-173G-175G-182R-199Y-216G-381C-420R;
22E-31H-56Q-124L-173G-175G-182R-199Y-381C-420R;
22E-31H-56Q-173G-175G-182R-199Y-216G-381C-420R;
22E-56Q-124L-173G-175G-182R-199Y-216G-381C-420R; or
22E-31H-56Q-124L-173G-175G-182R-199Y-216G-381C-420R, wherein the positions are numbered by reference to SEQ ID NO: 1.

In some embodiments, the modified GluDH further comprises substitutions of amino acids at one or more positions selected from positions 9, 23, 25, 143, 263, 339, 431 and 437. Preferably, the amino acid at position 9 is substituted with S, L or Y. Preferably, the amino acid at position 23 is substituted with M. Preferably, the amino acid at position 25 is substituted with D. Preferably, the amino acid at position 143 is substituted with E. Preferably, the amino acid at position 263 is substituted with S. Preferably, the amino acid at position 339 is substituted with Q. Preferably, the amino acid at position 431 is substituted with S. Preferably, the amino acid at position 437 is substituted with K.

The GluDH polypeptide, based on which the modification of amino acid is conducted, is referred to as the initiate GluDH herein. The initiate GluDH may be a wild-type GluDH, and may also be a variant of wild-type GluDH. For example, if the modification is initiated based on the polypeptide of SEQ ID NO: 1, the polypeptide of SEQ ID NO: 1 is the "initiate GluDH" with respect to the modified GluDH; and if the modification is initiated based on a variant polypeptide of SEQ ID NO: 1 (e.g., SEQ ID NO: 3-30), the variant polypeptide is the "initiate GluDH" with respect to the modified GluDH.

As used herein, the term "wild-type GluDH" refers to the naturally occurring GluDH. In some embodiments, the initial GluDH is the GluDH derived from a microorganism of Bacillaceae. In some embodiments, the wild-type GluDH is a GluDH from a microorganism of the genus *Lysinibacillus* or *Bacillus*. Preferably, the wild-type GluDH is a GLuDH from *Lysinibacillus sphaericus* (SEQ ID NO: 2) or a GluDH from *Bacillus velezensis* (SEQ ID NO: 1).

For the present invention, in order to determine the percentage identity between two amino acid sequences or two nuleic acid sequences, the sequences are aligned for the purpose of optimal comparison (e.g., a gap can be introduced into the first amino acid or nucleic acid sequence for the optimal alignment with the second amino acid or nucleic acid sequence). Then, the amino acid residues or nucleotides at the corresponding amino acid positions or nucleotide position are compared. When a position in the first sequence is occupied by the same amino acid residue or nucleotide at the corresponding position in the second sequence, these molecules are identical at this position. The percentage identity between two sequences is a function of the number of identical positions shared by the sequences (i.e., percentage identity=number of identical positions/total number of positions (i.e., the overlapping positions)×100). Preferably, the two sequences are idnetical in length.

A person skilled in the art knows that various computer programs can be used to determine the identity between two sequences.

"Amino acid identity percentage" or "amino acid sequence identity percentage" refers to the comparison between the amino acids of two polypeptides, and when optimally aligned, the two polypeptides have approximately the specified percentage of identical amino acids. For example, "95% amino acid identity" refers to the comparison between the amino acids of two polypeptides, and when optimally aligned, 95% of the amino acids of the two polypeptides are identical.

In some embodiment, the wild-type GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH, as compared to the initial GluDH thereof, has the following combinations of substitutions of amino acids:

the amino acid at position 104 is substituted with C, and the amino acid at position 175 is substituted with G;

the amino acid at position 132 is substituted with L, and the amino acid at position 175 is substituted with G;

the amino acid at position 133 is substituted with V, and the amino acid at position 175 is substituted with G;

the amino acid at position 173 is substituted with G or S, and the amino acid at position 175 is substituted with G;

the amino acid at position 175 is substituted with G, and the amino acid at position 181 is substituted with K or R;

the amino acid at position 175 is substituted with G, and the amino acid at position 182 is substituted with R;

the amino acid at position 175 is substituted with G, and the amino acid at position 203 is substituted with I;

the amino acid at position 132 is substituted with L, the amino acid at position 133 is substituted with V, and the amino acid at position 175 is substituted with G;

the amino acid at position 132 is substituted with L, the amino acid at position 173 is substituted with S, and the amino acid at position 175 is substituted with G;

the amino acid at position 132 is substituted with L, the amino acid at position 175 is substituted with G, and the amino acid at position 182 is substituted with R;

the amino acid at position 133 is substituted with V, the amino acid at position 173 is substituted with G or S, and the amino acid at position 175 is substituted with G;

the amino acid at position 133 is substituted with V, the amino acid at position 175 is substituted with G, and the amino acid at position 182 is substituted with R;

the amino acid at position 173 is substituted with G, the amino acid at position 175 is substituted with G, and the amino acid at position 182 is substituted with R;

the amino acid at position 132 is substituted with L, the amino acid at position 133 is substituted with V, the amino acid at position 173 is substituted with S, and the amino acid at position 175 is substituted with G;

the amino acid at position 132 is substituted with L, the amino acid at position 133 is substituted with V, the amino acid at position 175 is substituted with G, and the amino acid at position 182 is substituted with R;

the amino acid at position 132 is substituted with L, the amino acid at position 173 is substituted with S, the amino acid at position 175 is substituted with G, and the amino acid at position 182 is substituted with R;

the amino acid at position 133 is substituted with V, the amino acid at position 173 is substituted with G or S, the amino acid at position 175 is substituted with G, and the amino acid at position 182 is substituted with R; and the amino acid at position 132 is substituted with L, the amino acid at position 133 is substituted with V, the amino acid at position 173 is substituted with G or S, the amino acid at position 175 is substituted with G, and the amino acid at position 182 is substituted with R, wherein the positions are numbered by reference to SEQ ID NO: 1. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises substitutions at positions 132 and 175 as compared to the initial GluDH thereof, wherein the positions are numbered by reference to SEQ ID NO: 1. Preferably, the amino acid at position 132 is substituted with L, and the amino acid at position 175 is substituted with G. In some embodiments, the modified GluDH of the present invention further comprises substitutions at one or more positions selected from positions 104, 133, 173, 181 and 182 as compared to the initial GluDH thereof. In some embodiments, the amino acid at position 104 is substituted with C. In some embodiments, the amino acid at position 133 is substituted with V. In some embodiments, the amino acid at position 173 is substituted with G or S. In some embodiments, the amino acid at position 181 is substituted with K or R. In some embodiments, the amino acid at position 182 is substituted with R. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises substitutions at positions 133 and 175 as compared to the initial GluDH thereof, wherein the positions are numbered by reference to SEQ ID NO: 1. Preferably, the amino acid at position 133 is substituted with V, and the amino acid at position 175 is substituted with G. In some embodiments, the modified GluDH of the present invention further comprises substitutions at one or more positions selected from positions 104, 132, 173, 181 and 182 as compared to the initial GluDH thereof. In some embodiments, the amino acid at position 104 is substituted with C. In some embodiments, the amino acid at position 132 is substituted with L. In some embodiments, the amino acid at position 173 is substituted with G or S. In some embodiments, the amino acid at position 181 is substituted with K or R. In some embodiments, the amino acid at position 182 is substituted with R. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises substitutions at positions 173 and 175 as compared to the initial GluDH thereof, wherein the positions are numbered by reference to SEQ ID NO: 1. Preferably, the amino acid at position 173 is substituted with G or S, and the amino acid at position 175 is substituted with G. In some embodiments, the modified GluDH of the present invention further comprises substitutions at one or more positions selected from positions 104, 132, 133, 181 and 182 as compared to the initial GluDH thereof. In some embodiments, the amino acid at position 104 is substituted with C. In some embodiments, the amino acid at position 132 is substituted with L. In some embodiments, the amino acid at position 133 is substituted with V. In some embodiments, the amino acid at position 181 is substituted with K or R. In some embodiments, the amino acid at position 182 is substituted with R. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises substitutions at positions 175 and 182 as compared to the initial GluDH thereof, wherein the positions are numbered by reference to SEQ ID NO: 1. Preferably, the amino acid at position 175 is substituted with G, and the amino acid at position 182 is substituted with R. In some embodiments, the modified GluDH of the present invention further comprises substitutions at one or more positions selected from positions 104, 132, 133, 173 and 181 as compared to the initial GluDH thereof. In some embodiments, the amino acid at position 104 is substituted with C. In some embodiments, the amino acid at position 132 is substituted with L. In some embodiments, the amino acid at position 133 is substituted with V. In some embodiments, the amino acid at position 173 is substituted with G or S. In some embodiments, the amino acid at position 181 is substituted with K or R. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises substitutions at positions 132, 133 and 175 as compared to the initial GluDH thereof, wherein the positions are numbered by reference to SEQ ID NO: 1. Preferably, the amino acid at position 132 is substituted with L, the amino acid at position 133 is substituted with V, and the amino acid at position 175 is substituted with G. In some embodiments, the modified GluDH of the present invention further comprises substitutions at one or more positions selected from positions 104, 173, 181 and 182 as compared to the initial GluDH thereof. In some embodiments, the amino acid at position 104 is substituted with C. In some embodiments, the amino acid at position 173 is substituted with G or S. In some embodiments, the amino acid at position 181 is substituted with K or R. In some embodiments, the amino acid at position 182 is substituted with R. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises substitutions at positions 132, 173 and 175 as compared to the initial GluDH thereof, wherein the positions are numbered by reference to SEQ ID NO: 1. Preferably, the amino acid at position 132 is substituted with L, the amino acid at position 173 is substituted with G or S, and the amino acid at position 175 is substituted with G. In some embodiments, the modified GluDH of the present invention further comprises substitutions at one or more positions selected from positions 104, 133, 181 and 182 as compared to the initial GluDH thereof. In some embodiments, the amino acid at position 104 is substituted with C. In some embodiments, the amino acid at position 133 is substituted with V. In some embodiments, the amino acid at position 181 is substituted with K or R. In some embodiments, the amino acid at position 182 is substituted with R. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises substitutions at positions 133, 173 and 175 as compared to the initial GluDH thereof, wherein the positions are numbered by reference to SEQ ID NO: 1. Preferably, the amino acid at position 133 is substituted with V, the amino acid at position 173 is substituted with G or S, and the amino acid at position 175 is substituted with G. In some embodiments, the modified GluDH of the present invention further comprises substitutions at one or more positions selected from positions 104, 132, 181 and 182 as compared to the initial GluDH thereof. In some embodiments, the amino acid at position 104 is substituted with C. In some embodiments, the amino acid at position 132 is substituted with L. In some embodiments, the amino acid at position 181 is substituted with K or R. In some embodiments, the amino acid at position 182 is substituted with R. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises substitutions at positions 132, 175 and 182 as compared to the initial GluDH thereof, wherein the positions are numbered by reference to SEQ ID NO: 1. Preferably, the amino acid at position 132 is substituted with L, the amino acid at position 175 is substituted with G, and the amino acid at position 182 is substituted with R. In some embodiments, the modified GluDH of the present invention further comprises substitutions at one or more positions selected from positions 104, 133, 173 and 181 as compared to the initial GluDH thereof. In some embodiments, the amino acid at position 104 is substituted with C. In some embodiments, the amino acid at position 133 is substituted with V. In some embodiments, the amino acid at position 173 is substituted with G or S. In some embodiments, the amino acid at position 181 is substituted with K or R. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises substitutions at positions 133, 175 and 182 as compared to the initial GluDH thereof, wherein the positions are numbered by reference to SEQ ID NO: 1. Preferably, the amino acid at position 133 is substituted with V, the amino acid at position 175 is substituted with G, and the amino acid at position 182 is substituted with R. In some embodiments, the modified GluDH of the present invention further comprises substitutions at one or more positions selected from positions 104, 132, 173 and 181 as compared to the initial GluDH thereof. In some embodiments, the amino acid at position 104 is substituted with C. In some embodiments, the amino acid at position 132 is substituted with L. In some embodiments, the amino acid at position 173 is substituted with G or S. In some embodiments, the amino acid at position 181 is substituted with K or R. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises substitutions at positions 173, 175 and 182 as compared to the initial GluDH thereof, wherein the positions are numbered by reference to SEQ ID NO: 1. Preferably, the amino acid at position 173 is substituted with G or S, the amino acid at position 175 is substituted with G, and the amino acid at position 182 is substituted with R. In some embodiments, the modified GluDH of the present invention further comprises substitutions at one or more positions selected from positions 104, 132, 133 and 181 as compared to the initial GluDH thereof. In some embodiments, the amino acid at position 104 is substituted with C. In some embodiments, the amino acid at position 132 is substituted with L. In some embodiments, the amino acid at position 133 is substituted with V. In some embodiments, the amino acid at position 181 is substituted with K or R. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH comprises substitutions at positions 173, 175 and 182 as compared to the initial GluDH thereof, wherein the positions are numbered by reference to SEQ ID NO: 1. Preferably, the amino acid at position 173 is substituted with G, the amino acid at position 175 is substituted with G, and the amino acid at position 182 is substituted with R. In some embodiments, the modified GluDH further comprises substitutions of amino acids at one or more positions selected from positions 9, 22, 23, 25, 31, 56, 124, 143, 199, 216, 242, 263, 339, 420, 431 and 437. Preferably, the amino acid at position 9 is substituted with S, L or Y. Preferably, the amino acid at position 22 is substituted with W or E. Preferably, the amino acid at position 23 is substituted with M. Preferably, the amino acid at position 25 is substituted with D. Preferably, the amino acid at position 31 is substituted with H. Preferably, the amino acid at position 56 is substituted with Q. Preferably, the amino acid at position 124 is substituted with L. Preferably, the amino acid at position 143 is substituted with E. Preferably, the amino acid at position 199 is substituted with W or Y. Preferably, the amino acid at position 216 is substituted with G. Preferably, the amino acid at position 263 is substituted with S, the amino acid at position 339 is substituted with Q. Preferably, the amino acid at position 420 is substituted with R. Preferably, the amino acid at position 431 is substituted with S. Preferably, the amino acid at position 437 is substituted with K. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH comprises substitutions of amino acids at positions 22, 56, 173, 175, 182, 199 and 420. Preferably, the amino acid at position 22 is substituted with E. Preferably, the amino acid at position 56 is substituted with Q. Preferably, the amino acid at position 173 is substituted with G. Preferably, the amino acid at position 175 is substituted with G. Preferably, the amino acid at position 182 is substituted with R. Preferably, the amino acid at position 199 is substituted with Y. Preferably, the amino acid at position 420 is substituted with R. In some embodiments, the modified GluDH further comprises substitutions of amino acids at one or more positions selected from positions 31, 124 and 216. Preferably, the amino acid at position 31 is substituted with H. Preferably, the amino acid at position 124 is substituted with L. Preferably, the amino acid at position 216 is substituted with G. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH of the present invention comprises, as compared to the initial GluDH, substitutions of amino acids at positions 22, 56, 173, 175, 182, 199, 381 and 420, wherein the positions are numbered by reference to SEQ ID NO: 1, and wherein the modified GluDH, as compared to the initial GluDH, has an increased activity for catalyzing the reaction of 2-carbonyl-4-(hydroxymethylphosphono) butyric acid (PPO) with an amino donor to generate L-glufosinate, and/or has an improved stability, and/or has an increased Vmax, a decreased Km or an increased Vmax/Km. Preferably, the amino acid at position 22 is substituted with E. Preferably, the amino acid at position 56 is substituted with Q. Preferably, the amino acid at position 173 is substituted with G. Preferably, the amino acid at position 175 is substituted with G. Preferably, the amino acid at position 182 is substituted with R. Preferably, the amino acid at position 199 is substituted with Y. Preferably, the amino acid at position 381 is substituted with C. Preferably, the amino acid at position 420 is substituted with R. In some embodiments, the modified GluDH further comprises substitutions of amino acids at one or more positions selected from positions 31, 124 and 216. Preferably, the amino acid at position 31 is substituted with H. Preferably, the amino acid at position 124 is substituted with L. Preferably, the amino acid at position 216 is substituted with G. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2. For example, the initial GluDH comprises or consists of SEQ ID NO: 1.

In some embodiments, the modified GluDH of the present invention comprises, as compared to the initial GluDH, substitutions of amino acids:

22E-56Q-173G-175G-182R-199Y-381C-420R;
22E-31H-56Q-173G-175G-182R-199Y-381C-420R;
22E-56Q-124L-173G-175G-182R-199Y-381C-420R;
22E-56Q-173G-175G-182R-199Y-216G-381C-420R;
22E-31H-56Q-124L-173G-175G-182R-199Y-381C-420R;
22E-31H-56Q-173G-175G-182R-199Y-216G-381C-420R;
22E-56Q-124L-173G-175G-182R-199Y-216G-381C-420R; or
22E-31H-56Q-124L-173G-175G-182R-199Y-216G-381C-420R, wherein the positions are numbered by reference to SEQ ID NO: 1. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2. For example, the initial GluDH comprises or consists of SEQ ID NO: 1.

In some embodiments, the modified GluDH further comprises substitutions of amino acids at one or more positions selected from positions 9, 23, 25, 143, 263, 339, 431 and 437. Preferably, the amino acid at position 9 is substituted with S, L or Y. Preferably, the amino acid at position 23 is substituted with M. Preferably, the amino acid at position 25 is substituted with D. Preferably, the amino acid at position 143 is substituted with E. Preferably, the amino acid at position 263 is substituted with S. Preferably, the amino acid at position 339 is substituted with Q. Preferably, the amino acid at position 431 is substituted with S. Preferably, the amino acid at position 437 is substituted with K. Preferably, the initial GluDH has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2. For example, the initial GluDH comprises or consists of SEQ ID NO: 1.

In some embodiments, the modified GluDH of the present invention has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the initial GluDH differs from SEQ ID NO: 1 or 2 in comprising the substitution, deletion, insertion and/or addition of one or more amino acids. In some embodiments, the initial GluDH comprises conserved substitutions of one or more amino acids as compared to SEQ ID NO: 1 or 2. In some embodiments, the initial GluDH comprises the insertion or deletion of one or more amino acids as compared to SEQ ID NO: 1 or 2.

The term "conserved substitution" is also referred to as substitution by "homologous" amino acid residue, meaning a substitution in which an amino acid is replaced by an amino acid residue with a similar side chain, e.g., amino acids with a basic side chain (e.g. lysine, arginine and histidine), amino acids with an acidic side chain (e.g. aspartic acid, glutamic acid), amino acids with a non-charged polar side chain (e.g. glycine, asparagine, glutamine, serine, threonine, tyrosine, cysteine), amino acids with a non-polar side chain (e.g. alanine, valine, leucine, isoleucine, proline, phenylalanine, methionine, tryptophan), amino acids with a beta-branched side chain (e.g. threonine, valine, isoleucine) and amino acids with an aromatic side chain (e.g. tyrosine, phenylalanine, tryptophan, histidine).

Generally, a conserved substitution of amino acids results in minimal influence to the activity of the obtained protein. Such substitutions are described below. A conserved substitution is to replace an amino acid with an amino acid that is similar in size, hydrophobicity, charge, polarity, spatial characteristics, and aromaticity. When it is desired to precisely regulate the properties of a protein, the substitutions are generally conserved.

As used herein, "homologous" amino acid residues refer to amino acid residues with similar chemical properties, which are related to hydrophobicity, charge, polarity, steric characteristics, aromatic characteristics, etc. Examples of amino acids that are homologous to each other include lysine, arginine, and histidine, which are positively charged; glutamic acid and aspartic acid, which are negatively charged; glycine, alanine, valine, leucine, isoleucine, proline, and phenylalanine, which are hydrophobic; serine, threonine, cysteine, methionine, tryptophan, tyrosine, asparagine, glutamine, which are polar; phenylalanine, tyrosine, and tryptophan, which are Aromatic; serine and threonine, or glutamine and asparagine, or leucine and isoleucine, which have chemically similar side chain groups.

Examples of conservative amino acid substitutions in proteins include: Ala is substituted by Ser, Arg is substituted by Lys, Asn is substituted by Gln or His, Asp is substituted by Glu, Cys is substituted by Ser, Gln is substituted by Asn, Glu is substituted by Asp, Gly is substituted by Pro, His is substituted by Asn or Gln, Ile is substituted by Leu Or Val, Leu is substituted by Ile or Val, Lys is substituted by Arg or Gln, Met is substituted by Leu or Ile, Phe is substituted by Met, Leu or Tyr, Ser is substituted by Thr, Thr is substituted by Ser, Trp is substituted by Tyr, Tyr is substituted by Trp or Phe, and Val is substituted by Ile or Leu.

In some embodiments, the modified GluDH comprises or consists of one of SEQ ID NOs: 4-14, 16-19, 21, 22, 24, 25, 27-30, 32-48, 50, 51 and 53-72, or the modified GluDH comprises substitutions (e.g., conserved substitutions) of 1-10 amino acids as compared to one of SEQ ID NO: 4-14, 16-19, 21, 22, 24, 25, 27-30, 32-48, 50, 51 and 53-72, wherein the substitutions are at positions other than positions 9, 22, 23, 25, 31, 56, 104, 124, 132, 133, 143, 173, 175, 181, 182, 199, 203, 216, 242, 263, 339, 420, 431 and 437, wherein the modified GluDH has an increased activity for catalyzing the reaction of PPO with an amino donor to generate L-glufosinate, and/or has an improved dynamic property, e.g., an increased Vmax, a decreased Km or an increased Vmax/Km, as compared to the initial GluDH thereof. In some embodiments, the modified GluDH comprises substitutions (e.g., conserved substitutions) of 1, 2, 3, 4, 5, 6, 7, 8, 9, 10 or more amino acids as compared to one of SEQ ID NOs: 4-14, 16-19, 21, 22, 24, 25, 27-30, 32-48, 50, 51 and 53-72, wherein the substitutions are at positions other than positions 9, 22, 23, 25, 31, 56, 104, 124, 132, 133, 143, 173, 175, 181, 182, 199, 203, 216, 242, 263, 339, 420, 431 and 437. In some embodiments, the modified GluDH of the present invention has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

In some embodiments, the modified GluDH comprises or consists of one of SEQ ID NOs: 73-80, or the modified GluDH comprises substitutions (e.g., conserved substitutions) of 1-10 amino acids as compared to one of SEQ ID NO: 73-80, wherein the substitutions are at positions other than positions 22, 31, 56, 124, 173, 175, 182, 199, 216, 381 and 420, wherein the modified GluDH has an increased activity for catalyzing the reaction of PPO with an amino donor to generate L-glufosinate, and/or has an improved stability, and/or has an improved dynamic property, e.g., an increased Vmax, a decreased Km or an increased Vmax/Km, as compared to SEQ ID NO: 1, 3, 21 or 65. In some embodiments, the modified GluDH of the present invention has a sequence identity of at least 65% or 70%, preferably at least 75% or 80%, more preferably at least 85% or 90%, and particularly preferably at least 94%, 95%, 96%, 97%, 98% or 99% to SEQ ID NO: 1 or 2.

As used herein, the activity of an enzyme refers to a decrease in the substrate or an increase in the product per unit time in a chemical reaction catalyzed by the enzyme in unit mass under certain conditions. For example, the activity of the modified GluDH of the present invention can be expressed by the amount of the decrease in PPO or the increase in L-glufosinate per unit time under the catalysis of unit mass of modified GluDH under certain conditions.

The activity of an enzyme herein can also refer to the relative activity of the enzyme, expressed as the ratio of the activity of the enzyme of interest to the activity of a given enzyme that catalyzes the same reaction, such as percentage relative activity.

In some embodiments, the activity of the modified GluDH of the present invention is expressed as the percentage relative activity as compared to SEQ ID NO: 3. In some embodiments, the activity of the modified GluDH on catalyzing the reaction of PPO with an amino donor to generate L-glufosinate is at least 100%, 105%, 110%, 120%, 130%, 140%, 150%, 160%, 170%, 180%, 190%, 200%, 250%, 300%, 350%, 400%, 450% or more of the activity of SEQ ID NO: 3 on catalyzing the reaction.

In some embodiments, the activity of the modified GluDH of the present invention is expressed as the percentage relative activity as compared to SEQ ID NO: 31. In some embodiments, the activity of the modified GluDH on catalyzing the reaction of PPO with an amino donor to generate L-glufosinate is at least 100%, 105%, 110%, 120%, 130%, 140%, 150%, 160%, 170%, 180%, 190%, 200% or more of the activity of SEQ ID NO: 31 on catalyzing the reaction.

As used herein, the term "amino donor" refers to a compound that provides an amino group, comprising an inorganic compound and an organic compound. An "amino donor" includes but is not limited to an ammonium salt (e.g., $NH_4Cl$, $NH_4NO_3$, $(NH_4)_2SO_4$, ammonium acetate, etc.), an amino acid or an organic amine. In some embodiment, the amino donor is an ammonium salt, e.g., $NH_4Cl$.

In addition to the activity of the enzyme, the stability and the dynamic properties need to be taken into account in the production.

The improved stability herein includes an increased stability. In some embodiments of the invention, the stability of an enzyme is thermostability, which means the property that the acitivity does not decrease or decreases with a small extent after an incubation at a certain temperature (e.g., 40-60° C. or higher) for a certain time period (e.g., 10 min to 1 hour). Taking the modified glutamate dehydrogenase (mGluDH) as an example, if the initial activity of mGluDH A is A1, and the activity thereof after an incubation at 43° C. for 20 min is A2; the initial activity of mGluDH B is B1, and the activity thereof after an incubation at 43° C. for 20 min is B2, when A1/A2 is greater than B1/B2, the thermostability of mGluDH B is higher than mGluDH A.

The dynamic properties of an enzyme herein include, but are not limited to, the Vmax, Km and Vmax/Km of the enzyme. An improved dynamic property herein includes, but is not limited to, an increased Vmax, a decreased Km and an increased Vmax/Km.

As used herein, the term "Vmax" refers to the maximum velocity of catalyzing a reaction that can be achieved with a certain concentration of an enzyme. In particular, under the condition with a constant concentration of an enzyme, the velocity of the reaction generally increases with the increase in the concentration of the substrate when the concentration of the substrate is within a certain range; the velocity of the reaction will reach the maximum value when the concentration of the substrate reaches a certain value, and the velocity of the reaction will not increase with the increase in the concentration of the substrate.

As used herein, the term "Km" refers to the concentration of the substrate, at which the velocity of the reaction reaches a half of the maximum velocity of catalysis, i.e., Vmax, with a certain concentration of enzyme.

II. The Polynucleotide Encoding the Modified GluDH

As used herein, the term "polynucleotide" or "nucleic acid molecule" includes DNA molecules (e.g. cDNA or genomic DNA) and RNA molecules (e.g. mRNA) and analogs of DNA or RNA produced using nucleotide analogs. The nucleic acid molecule may be single-stranded or double-stranded, preferably double-stranded DNA. The synthesis of the nucleic acid can use nucleotide analogs or derivatives (for example, inosine or phosphorothioate nucleotides). Such nucleotides can be used, for example, to prepare nucleic acids with altered base pairing ability or increased nuclease resistance.

The present invention also provides a polynucleotide encoding the modified GluDH of the present invention. Therefore, in the present invention, the term modification also includes genetic manipulation of the polynucleotide encoding the GluDH polypeptide of the present invention. The modification can be substitution, deletion, insertion and/or addition of one or more nucleotides.

As used herein, the term "encoding" means that a polynucleotide directly specifies the amino acid sequence of its protein product. The boundaries of the coding sequence are generally determined by an open reading frame, which generally starts with the ATG start codon or other start codons such as GTG and TTG, and ends with a stop codon such as TAA, TAG and TGA. The coding sequence can be a DNA, cDNA or recombinant nucleotide sequence.

In addition, nucleic acid molecules covering all or part of the nucleic acid sequence of the present invention can be isolated by polymerase chain reaction (PCR), using oligonucleotide primers which are designed and synthesized based on the sequence information comprised in the sequence.

The polynucleotide of the present invention can be amplified with cDNA, mRNA or genomic DNA as the template and suitable oligonucleotide primers according to standard PCR amplification techniques. The nucleic acid amplified as above can be cloned into a suitable vector and characterized by DNA sequence analysis.

The polynucleotide of the present invention can be prepared by standard synthesis techniques, for example, by using an automated DNA synthesizer.

The present invention also relates to the complementary strand of the nucleic acid molecule described herein. A nucleic acid molecule that is complementary to other nucleotide sequence is a molecule that is sufficiently complementary to the nucleotide sequence so that it can hybridize with the other nucleotide sequences to form a stable duplex.

As used herein, the term "hybridization" that nucleotides sequences, which are at least about 90%, preferably at least about 95%, more preferably at least about 96%, and more preferably at least 98% homologous to each other, generally maintain hybridization with each other under given stringent hybridization and washing conditions.

A person skilled in the art knows various conditions for hybridization, such as stringent hybridization conditions and highly stringent hybridization conditions. See, for example, Sambrook et al., 1989, Molecular Cloning, A Laboratory Manual, Cold Spring Harbor Press, N.Y.; and Ausubel et al. (eds.), 1995, Current Protocols in Molecular Biology, John Wiley & Sons, N.Y..

Of course, the polynucleotide of the present invention does not include a polynucleotide that only hybridizes to a poly A sequence (such as the 3' end poly(A) of mRNA) or a complementary stretch of poly T (or U) residues.

III. The Expression and Production of the Modified GluDH

In order to express the modified GluDH of the present invention, also provided is a nucleic acid construct and a vector comprising the polynucleotide of the present invention, such as an expression vector.

As used herein, the term "expression" includes any step involved in the production of a polypeptide, including but not limited to transcription, post-transcriptional modification, translation, post-translational modification, and secretion.

The term "nucleic acid construct" refers to a single-stranded or double-stranded nucleic acid molecule, which is isolated from a naturally occurring gene or modified to contain a nucleic acid segment that does not naturally occur. When the nucleic acid construct contains the control sequences required to express the coding sequence of the present invention, the term nucleic acid construct is synonymous with the term "expression cassette".

The term "expression vector" refers herein to a linear or circular DNA molecule comprising a polynucleotide encoding the polypeptide of the present invention operably linked to additional nucleotides provided for the expression of the polynucleotide, for example, control sequence. The expression vector includes a viral vector or a plasmid vector.

The term "control sequence" herein includes all elements necessary or beneficial for the expression of the polynucleotide encoding the polypeptide of the present invention. Each control sequence may be natural or foreign to the nucleotide sequence encoding the polypeptide, or natural or foreign to each other. Such control sequences include, but are not limited to, leader sequence, polyadenylation sequence, propeptide sequence, promoter, signal peptide sequence, and transcription terminator. At a minimum, control sequences include a promoter and signals for the termination of transcription and translation.

For example, the control sequence may be a suitable promoter sequence, a nucleotide sequence recognized by the host cell to express the polynucleotide encoding the polypeptide of the present invention. The promoter sequence contains a transcription control sequence that mediates the expression of the polypeptide. The promoter may be any nucleotide sequence that exhibits transcriptional activity in the selected host cell, for example, lac operon of *E. coli*. The promoters also include mutant, truncated and hybrid promoters, and can be obtained from genes encoding extracellular or intracellular polypeptides, which are homologous or heterologous to the host cell.

The term "operably linked" herein refers to a configuration in which a control sequence is placed at an appropriate position relative to the coding sequence of the polynucleotide sequence, whereby the control sequence directs the expression of the polypeptide coding sequence.

The polynucleotide encoding the polypeptide of the present invention can be subjected to various manipulations to allow the expression of the polypeptide. Before the insertion thereof into a vector, manipulation of the polynucleotide according to the expression vector is desirable or necessary. Techniques for modifying polynucleotide sequences with recombinant DNA methods are well known in the art.

In order to identify and select host cells comprising the expression vector of the present invention, the vector of the present invention preferably contains one or more selectable markers, which allow simple selection of transformed, transfected, transduced, etc. cells. A selectable marker is a gene, of which the product provides biocide or virus resistance, heavy metal resistance, supplemental auxotrophs, etc. For example, the bacterial selectable marker is the dal gene from *Bacillus subtilis* or *Bacillus licheniformis*, or a marker that confers antibiotic resistance such as ampicillin, kanamycin, chloramphenicol or tetracycline resistance.

The vector of the present invention can be integrated into the genome of the host cell or autonomously replicate in the cell, which is independent of the genome. The elements required for the integration into the genome of the host cell or the autonomous replication are known in the art (see, for example, the aforementioned Sambrook et al., 1989).

Vector DNA can be introduced into prokaryotic or eukaryotic cells by conventional transformation or transfection techniques. As used herein, the terms "transformation" and "transfection" refer to various techniques for introducing foreign nucleic acids (such as DNA) into host cells, which are well known in the art, and can be found in, for example, the aforementioned Sambrook et al., 1989; Davis et al., Basic Methods in Molecular Biology (1986) and other laboratory manuals.

The present invention also relates to a recombinant host cell comprising the polynucleotide of the present invention, which is advantageously used in the recombinant production of GluDH polypeptides. The vector comprising the polynucleotide of the present invention is introduced into the host cell, whereby the vector is retained as a chromosomal integrant or as a self-replicating extrachromosomal vector. A person skilled in the art knows the conventional vectors and host cells for expressing proteins.

In some embodiments, the host cell of the present invention is an *E. coli* cell, such as *E. coli* BL21 (DE3). In some embodiments, the expression vector is pET-30a(+).

The modified GluDH of the present invention can be operably linked to a non-GluDH polypeptide (for example, a heterologous amino acid sequence) to form a fusion protein. For example, in one embodiment, the fusion protein is a GST-GluDH fusion protein, wherein the GluDH sequence is fused to the C-terminus of the GST sequence. This fusion protein can facilitate the purification of recombinant GluDH. In another embodiment, the fusion protein is a GluDH protein containing a heterologous signal sequence at its N-terminus. In certain host cells (e.g., mammalian and yeast host cells), the expression and/or secretion of GluDH can be increased by the use of a heterologous signal sequence.

IV. The Production of L-Glufosinate

Moreover, the present invention provides a method for preparing L-glufosinate comprising contacting the modified GluDH or the host cell of the present invention with PPO.

In some embodiments, the method for preparing L-glufosinate-ammonium of the present invention comprises the steps of:

(a) providing the activity of the modified GluDH of the present invention to a reaction medium comprising PPO and an amino donor, optionally, the reaction medium comprises NADPH/NADP cycling system, and (b) incubating the reaction medium to generate L-glufosinate.

In some embodiments, a cell-free-catalysis method is used to produce L-glufosinate, and the modified GluDH of the present invention is provided in step (a). In some embodiments, the modified GluDH of the invention which is free or immobilized can be used.

In some embodiments, the amino donor is an ammonium salt, e.g., $NH_4Cl$.

In some embodiments, the reaction medium comprises NADPH/NADP. An NADPH/NADP cycling system suitable for the present invention is known in the art, which comprises, but is not limited to, an alcohol dehydrogenase, a glucose dehydrogenase (GDH), or a glucose-6-phosphate dehydrogenase (G6PD). In some embodiments, the NADPH/NADP cycling system comprises an alcohol dehydrogenase. In some embodiments, the alcohol dehydrogenase can also be immobilized.

In some embodiments, the incubation is performed at 20-50° C., preferably 25-40° C., more preferably 28-35° C., e.g., 30° C.

In some embodiments, the medium is a buffer, such as PBS, and Tris-HCl buffer. In one embodiment, the medium is a PBS buffer, such as a PBS buffer of 100 mM. In some embodiments, the pH of the reaction medium is 7.5-8.

In some embodiments, the reaction medium is a medium partially or entirely composed of cell culture medium, and the activity of the modified GluDH of the present invention is provided by the host cell of the present invention, which is cultured in the reaction medium.

In some embodiments, the reaction medium is a medium partially or entirely composed of cell culture medium, and the NADPH/NADP cycling system, such as the alcohol dehydrogenase activity is provided by the host cell of the present invention or by a second host cell, which is cultured in the reaction medium.

In some embodiments, the host cell of the present invention and/or the second host cell are cultured and expanded in a cell culture medium, and then, the expanded host cells are separated from the cell culture medium, and a buffer or water is used to resuspend the biomass. PPO is provided to the buffer or water before, during or after the addition of the expanded host cells.

In some embodiments, bacterial cells can be used, such as *E. coli* cells.

EXAMPLES

A person skilled in the art will understand the present invention more clearly through the following examples. It should be understood that the examples are for illustration only, rather than limiting the scope of the present invention.

Example 1. Materials and Methods

Unless otherwise specified, the experimental methods used in the present invention are all conventional methods. The particular gene cloning operation can be seen in the aforementioned Sambrook et al., 1989.

i) Reagents

DNA polymerase (PrimeSTAR Max DNA Polymerase) and DpnI endonuclease were purchased from TaKaRa; plasmid isolation kit was purchased from Axygen; PPO was synthesized by the Applicant according to the prior art (see *J. Org. Chem.* 1991, 56, 1783-1788); $NH_4Cl$ was purchased from Sinopharm Chemical Reagent Co. Ltd., Beijing; NADP+/NADPH was purchased from Aladdin; the alcohol dehydrogenase is a dehydrogenase from *Lactobacillus kefiri* (NCBI accession No. WP_054768785.1), which is recombinantly expressed in *E. coli.* ii) Vectors and Strains

The expression vector used was pET-30a(+), the plasmid was purchased from Novagen;

and the host cell used was *E. coli* BL21 (DE3), purchased from Tiangen BioTech (Beijing) Co., Ltd.

iii) Sequencing and Primer Synthesis were Accomplished by Synbio Technologies Co., Ltd.

iv) Site-Directed Mutation

Specific primer pairs were designed to introduce the desired substitutions at the bases corresponding to the amino acid positions that are needed to be mutated. The isolated pre-mutation plasmid (comprising the coding sequence for the wild-type GluDH, and pET-30a(+) backbone) was used as the template, and mutations were introduced by PCR using Quickchange technology (Nucleic Acids Research, 2004, 32 (14): e115). After PCR amplification, the amplified product was digested with DpnI for 4 h to remove the template plasmid. The digested product was transformed into *E. coli* BL21 (DE3) competent cells, followed by spreading the cells on LB agar (containing 50 mg/L kanamycin), inoculating single colonies into LB broth (containing 50 mg/L kanamycin) for culture, and sequencing to verify the correct mutants. The verified clone is stored at −80° C. for future use.

v) Protein Expression and the Preparation of Crude Enzyme Solution

The stored clones were activated on LB agar. Then, single colonies were inoculated into LB broth (containing 50 mg/L kanamycin), and incubated at 37° C. with shaking for 12 h. 1 mL culture was transferred to 50 mL fresh LB broth (containing 50 mg/L kanamycin), incubated with shaking at 37° C. until OD600 reaches about 0.6, and incubated at 25° C. for 16 h to induce protein expression after the addition of IPTG (final concentration of 0.4 mM).

After the incubation, the culture was centrifuged at 4,000 g for 10 min at 4° C., the supernatant was discarded, and *E. coli* cells were collected. The collected *E. coli* cells were resuspended in 15 mL pre-chilled PBS of 50 mM, pH 7.0, and were sonicated at 4° C. for disruption. The cell disruption solution was centrifuged at 6,000 g at 4° C. for 15 min to remove the precipitate, and the supernatant obtained was the crude enzyme solution containing the recombinant enzyme.

vi) Determination of the Enzyme Activity

The $NH_4Cl$ and NADP+ were added to the solution of PPO in PBS (100 mM), and the pH of the solution was adjusted to 8 with aqueous ammonia solution. The solution comprises PPO at a final concentration of 100 mM, $NH_4Cl$ at a final concentration of 50 mM and NADP+ at a final concentration of 0.2 g/L. The crude enzyme solution obtained as described in v) and the alcohol dehydrogenase were added to the above solution. The final concentration of GluDH is 0.02 g/L, and the final concentration of the alcohol dehydrogenase is 0.2 g/L. The solution was kept shaking (400 rpm) on a shaker at 30° C. for 2 hours, and then, sampled for detecting the amount of the generated L-glutamine with OPA pre-column derivating HPLC, thereby determining the initial velocity of the catalyzed reaction.

vii) Determination of the Dynamic Properties of the Enzyme

A plurality of reaction systems (200 μL) comprising PBS of 100 mM pH 7.5 (pH was adjusted with aqueous ammonia solution), NADPH (reductive) of 0.15 mM, $NH_4Cl$ of 50 mM, diluted (500 folds) crude enzyme solution of 10% volume and the substrate PPO at various concentrations (5-100 mM) were formulated on a 96-well plate. The intensity of the UV absorption at 340 nm was detected at 30° C., and the rate of change in absorption over time (mA/min) was recorded. The obtained parameters were plugged into Michaelis-Menten equation, in which the reaction velocity was calculated with the rate of change in absorption.

Example 2. The Preparation and Detection of Mutants of GluDH from *Bacillus velezensis* (BvGluDH)

The mutants were prepared with the coding nucleic acid of BvGluDH (SEQ ID NO: 1) as the template, and the enzyme activities and the dynamic parameters Vmax and Km were measured, according to the method of Example 1. The resulted mutants and the enzyme activities and the dynamic parameters thereof are shown in Table 1, and the relative enzyme activity means the percentage of the enzyme activity of the mutant to the enzyme activity of the mutant of SEQ ID NO: 3.

TABLE 1

| Substitutions introduced in the mutant | SEQ ID NO: | Relative enzyme activity | Vmax (mA/min) | Km (mM) |
|---|---|---|---|---|
| A175G | 3 | 100% | 60 | 73 |
| A175G-L104C | 4 | 90% | 60 | 34 |
| A175G-P132L | 5 | 131% | 56 | 32 |
| A175G-I133V | 6 | 113% | 59 | 43 |
| A175G-V173S | 7 | 111% | 79 | 52 |
| A175G-V173G | 8 | 123% | 80 | 53 |
| A175G-G181K | 9 | 93% | 70 | 80 |
| A175G-G181R | 10 | 100% | 77 | 84 |
| A175G-A182R | 11 | 111% | 61 | 46 |
| A175G-V203I | 12 | 72% | 53 | 62 |
| A175G-P132L-I133V | 13 | 131% | 34 | 41 |
| A175G-P132L-V173S | 14 | 132% | 53 | 26 |
| A175G-P132L-V173G | 15 | 61% | 22 | 36 |
| A175G-P132L-A182R | 16 | 115% | 36 | 29 |
| A175G-I133V-V173S | 17 | 178% | 78 | 51 |
| A175G-I133V-V173G | 18 | 164% | 54 | 71 |
| A175G-I133V-A182R | 19 | 112% | 49 | 26 |
| A175G-V173S-A182R | 20 | 35% | 10 | 56 |
| A175G-V173G-A182R | 21 | 160% | 71 | 23 |
| A175G-P132L-I133V-V173S | 22 | 95% | 46 | 32 |
| A175G-P132L-I133V-V173G | 23 | 53% | 14 | 47 |
| A175G-P132L-I133V-A182R | 24 | 97% | 39 | 35 |
| A175G-P132L-V173S-A182R | 25 | 79% | 40 | 14 |
| A175G-P132L-V173G-A182R | 26 | 34% | 19 | 22 |
| A175G-I133V-V173S-A182R | 27 | 139% | 65 | 28 |
| A175G-I133V-V173G-A182R | 28 | 139% | 73 | 26 |
| A175G-P132L-I133V-V173S-A182R | 29 | 70% | 37 | 24 |
| A175G-P132L-I133V-V173G-A182R | 30 | 138% | 71 | 53 |

Example 3. The Preparation and Detection of Mutants of GluDH from *Lysinibacillus sphaericus* (LsGluDH)

The mutants were prepared with the coding nucleic acid of LsGluDH (SEQ ID NO: 2) as the template, and the enzyme activities and the dynamic parameters Vmax and Km were measured, according to the method of Example 1. The resulted mutants and the enzyme activities and the dynamic parameters thereof are shown in Table 2, and the relative enzyme activity means the percentage of the enzyme activity of the mutant to the enzyme activity of the mutant of SEQ ID NO: 31.

TABLE 2

| Substitutions introduced in the mutant | SEQ ID NO: | Relative enzyme activity | Vmax (mA/min) | Km (mM) |
|---|---|---|---|---|
| A175G | 31 | 100% | 39 | 49 |
| A175G-P132L | 32 | 127% | 45 | 35 |
| A175G-I133V | 33 | 106% | 39 | 35 |
| A175G-V173S | 34 | 185% | 106 | 62 |
| A175G-V173G | 35 | 132% | 64 | 49 |
| A175G-A182R | 36 | 102% | 46 | 38 |
| A175G-V173G-A182R | 37 | 169% | 58 | 31 |
| A175G-I133V-V173S-A182R | 38 | 131% | 38 | 26 |

Example 4. The Preparation and Detection of Mutants of BvGluDH

The mutants were prepared by introducing additional mutations based on the mutant of SEQ ID NO: 21, and the enzyme activities were measured, according to the method of Example 1. The resulted mutants and the enzyme activities thereof are shown in Table 3, and the initial relative enzyme activity means the percentage of the enzyme activity of the mutant to the enzyme activity of the mutant of SEQ ID NO: 21 without thermo-treatment; and the relative enzyme activity after thermo-treatment means the percentage of the enzyme activity of the mutant to the enzyme activity of the mutant of SEQ ID NO: 21 after incubating at 45° C. for 30 min.

TABLE 3

| Substitutions introduced in the mutant | SEQ ID NO: | Initial relative enzyme activity | Relative enzyme activity after thermo-treatment |
|---|---|---|---|
| A175G-V173G-A182R | 21 | 100% | 100% |
| A175G-V173G-A182R-Q22W | 39 | 106% | 143% |
| A175G-V173G-A182R-Q22E | 40 | 114% | 140% |
| A175G-V173G-A182R-L23M | 41 | 153% | 158% |
| A175G-V173G-A182R-K56Q | 42 | 104% | 145% |
| A175G-V173G-A182R-D9S | 43 | 113% | 95% |
| A175G-V173G-A182R-D9L | 44 | 108% | 122% |
| A175G-V173G-A182R-D9Y | 45 | 86% | 82% |
| A175G-V173G-A182R-N25D | 46 | 105% | 117% |
| A175G-V173G-A182R-N199W | 47 | 142% | 201% |
| A175G-V173G-A182R-N199Y | 48 | 133% | 197% |
| A175G-V173G-A182R-D242G | 49 | 57% | 88% |
| A175G-V173G-A182R-N143E | 50 | 90% | 111% |
| A175G-V173G-A182R-A263S | 51 | 103% | 87% |
| A175G-V173G-A182R-A263K | 52 | 65% | 77% |
| A175G-V173G-A182R-D339Q | 53 | 119% | 81% |
| A175G-V173G-A182R-A420R | 54 | 139% | 170% |
| A175G-V173G-A182R-Y431S | 55 | 142% | 156% |
| A175G-V173G-A182R-V437K | 56 | 156% | 132% |
| A175G-V173G-A182R-K56Q-N199W | 57 | 160% | 171% |
| A175G-V173G-A182R-Q22E-N199W | 58 | 166% | 185% |
| A175G-V173G-A182R-K56Q-N199Y | 59 | 167% | 182% |
| A175G-V173G-A182R-Q22E-N199Y | 60 | 176% | 182% |
| A175G-V173G-A182R-K56Q-N199Y-A420R | 61 | 159% | 175% |
| A175G-V173G-A182R-Q22E-N199Y-A420R | 62 | 175% | 193% |
| A175G-V173G-A182R-Q22E-K56Q-N199Y | 63 | 172% | 195% |
| A175G-V173G-A182R-Q22E-K56Q-N199W | 64 | 161% | 172% |
| A175G-V173G-A182R-Q22E-K56Q-N199Y-A420R | 65 | 184% | 189% |

Example 5. The Preparation and Detection of Mutants of BvGluDH

The mutants were prepared by introducing additional mutations based on the mutant of SEQ ID NO: 65, and the enzyme activities were measured, according to the method of Example 1. The resulted mutants and the enzyme activities thereof are shown in Table 4, and the relative enzyme activity means the percentage of the enzyme activity of the mutant to the enzyme activity of the mutant of SEQ ID NO: 65.

TABLE 4

| Substitutions introduced in the mutant | SEQ ID NO: | Relative enzyme activity |
|---|---|---|
| A175G-V173G-A182R-Q22E-K56Q-N199Y-A420R | 65 | 100% |
| A175G-V173G-A182R-Q22E-K56Q-N199Y-A420R-A31H | 66 | 165% |
| A175G-V173G-A182R-Q22E-K56Q-N199Y-A420R-F124L | 67 | 106% |
| A175G-V173G-A182R-Q22E-K56Q-N199Y-A420R-A216G | 68 | 117% |
| A175G-V173G-A182R-Q22E-K56Q-N199Y-A420R-A31H-F124L | 69 | 143% |
| A175G-V173G-A182R-Q22E-K56Q-N199Y-A420R-A31H-A216G | 70 | 132% |
| A175G-V173G-A182R-Q22E-K56Q-N199Y-A420R-F124L-A216G | 71 | 97% |
| A175G-V173G-A182R-Q22E-K56Q-N199Y-A420R-A31H-F124L-A216G | 72 | 103% |
| A175G-V173G-A182R-Q22E-K56Q-N199Y-A420R-A381C | 73 | 116% |
| A175G-V173G-A182R-Q22E-K56Q-N199Y-A420R-A31H-A381C | 74 | 146% |
| A175G-V173G-A182R-Q22E-K56Q-N199Y-A420R-F124L-A381C | 75 | 154% |
| A175G-V173G-A182R-Q22E-K56Q-N199Y-A420R-A216G-A381C | 76 | 108% |
| A175G-V173G-A182R-Q22E-K56Q-N199Y-A420R-A31H-F124L-A381C | 77 | 101% |
| A175G-V173G-A182R-Q22E-K56Q-N199Y-A420R-A31H-A216G-A381C | 78 | 114% |
| A175G-V173G-A182R-Q22E-K56Q-N199Y-A420R-F124L-A216G-A381C | 79 | 163% |
| A175G-V173G-A182R-Q22E-K56Q-N199Y-A420R-A31H-F124L-A216G-A381C | 80 | 157% |

The invention claimed is:

1. A modified glutamate dehydrogenase (GluDH), wherein the modified GluDH comprises an amino acid sequence having at least 95% sequence identity to the amino acid sequence of SEQ ID NO:1 or SEQ ID NO:2, wherein the modified GluDH comprises substitutions of amino acids corresponding to positions 22, 56, 173, 175, 182, 199, 381 and 420 of SEQ ID NO: 1 or 2, wherein the amino acid at position 22 is substituted with E, the amino acid at position 56 is substituted with Q, the amino acid at position 173 is substituted with G, the amino acid at position 175 is substituted with G, the amino acid at position 182 is substituted with R, the amino acid at position 199 is substituted with Y, the amino acid at position 381 is substituted with C, and the amino acid at position 420 is substituted with R, and wherein the modified GluDH catalyzes a reaction of 2-carbonyl-4-(hydroxymethylphosphono)butyric acid (PPO) with an amino donor to generate L-glufosinate.

2. The modified GluDH of claim 1, wherein the modified GluDH is derived from a wildtype GluDH.

3. The modified GluDH of claim 1, wherein the modified GluDH is derived from a *Lysinibacillus sphaericus* or *Bacillus velezensis* GluDH.

4. The modified GluDH of claim 1, wherein the modified GluDH is derived from a GluDH comprising the amino acid sequence of SEQ ID NO: 1 or 2.

5. The modified GluDH of claim 1, further comprising one or more substitutions of amino acids corresponding to one or more of positions 31, 124 and 216 of SEQ ID NO: 1 or 2, wherein the amino acid at position 31 is substituted with H, the amino acid at position 124 is substituted with L, and the amino acid at position 216 is substituted with G.

6. The modified GluDH of claim 1, further comprising one or more substitutions of amino acids corresponding to one or more of positions 9, 23, 25, 143, 263, 339, 431 and 437 of SEQ ID NO: 1 or 2, wherein the amino acid at position 9 is substituted with S, L or Y, the amino acid at position 23 is substituted with M, the amino acid at position 25 is substituted with D, the amino acid at position 143 is substituted with E, the amino acid at position 263 is substituted with S, the amino acid at position 339 is substituted with Q, the amino acid at position 431 is substituted with S, and the amino acid at position 437 is substituted with K.

7. The modified GluDH of claim 1, wherein the modified GluDH comprises the amino acid sequence of any one of SEQ ID NOs: 73-80.

8. A polynucleotide comprising a nucleotide sequence encoding the modified GluDH of claim 1.

9. An expression vector comprising the polynucleotide of claim 8.

10. A host cell comprising the modified GluDH of claim 1.

11. A method of producing L-glufosinate comprising contacting the modified GluDH of claim 1 with PPO.

12. A method of producing L-glufosinate comprising contacting the host cell of claim 10 with PPO.

* * * * *